United States Patent
O'Keefe et al.

(10) Patent No.: US 11,034,736 B2
(45) Date of Patent: Jun. 15, 2021

(54) ANTI-VIRAL CNIDARINS

(71) Applicant: The United States of America, as represented by the Secretary, Department of Health and Human Services, Bethesda, MD (US)

(72) Inventors: Barry R. O'Keefe, Frederick, MD (US); James B. McMahon, Frederick, MD (US); Koreen Ramessar, Herndon, VA (US); Chang-yun Xiong, Apex, NC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 211 days.

(21) Appl. No.: 15/110,156

(22) PCT Filed: Jan. 9, 2015

(86) PCT No.: PCT/US2015/010797
§ 371 (c)(1),
(2) Date: Jul. 7, 2016

(87) PCT Pub. No.: WO2015/106086
PCT Pub. Date: Jul. 16, 2015

(65) Prior Publication Data
US 2016/0333060 A1    Nov. 17, 2016

Related U.S. Application Data

(60) Provisional application No. 61/925,347, filed on Jan. 9, 2014.

(51) Int. Cl.
  *C07K 14/435* (2006.01)
  *C07K 16/18* (2006.01)
  *A61K 38/17* (2006.01)
  *A61K 38/00* (2006.01)
  *A61K 48/00* (2006.01)

(52) U.S. Cl.
  CPC .... *C07K 14/43595* (2013.01); *A61K 38/1767* (2013.01); *C07K 14/435* (2013.01); *C07K 16/18* (2013.01); *A61K 38/00* (2013.01); *A61K 48/00* (2013.01)

(58) Field of Classification Search
  CPC .............. C07K 14/43595; A61K 38/1767
  See application file for complete search history.

(56) References Cited

FOREIGN PATENT DOCUMENTS

| WO | WO 2005/118627 A2 | 12/2005 |
|---|---|---|
| WO | WO 2006/127822 A2 | 11/2006 |

OTHER PUBLICATIONS

UniProt [Online] Oct. 16, 2013 (Oct. 16, 2013), SubName: Full=WRKY transcription factor 43.2 {ECO:0000313|EMBL: AGQ04234.1}; retrieved from EBI accession No. UNIPROT:S5CH60 Database accession No. S5CH60.*
Reina, J. J., et al., 2010, HIV microbicides: state-of-the-art and new perspectives on the development of entry inhibitors, Future Medicinal Chem. 2(7):1141-1159.*
Morris, G. C., and C. J. N. Lacey, 2010, Microbicides and HIV prevention: lessons from the past, looking to the future, Curr. Opin. Infect. Dis. 23:57-63.*
Balzarini, "Inhibition of HIV entry by carbohydrate-binding proteins," *Antiviral Res.*, 71 (2-3), 237-247 (2006).
EBI Accession No. AEL93634 (dated Jan. 11, 2007).
Ellithey et al., "Cytotoxic and HIV-1 enzyme inhibitory activities of Red Sea marine organisms," *BMC Complement. Altern. Med.*, 14, 77 (2014).
Ellithey et al., "Cytotoxic, cytostatic and HIV-1 PR inhibitory activities of the soft coral *Litophyton arboreum*," *Mar. Drugs*, 11 (12), 4917-4936 (2013).
GenBank Accession No. ABV24985 (dated Sep. 18, 2007).
GenBank Accession No. EGD92815.1 (dated Mar. 12, 2015).
International Search Report, Application No. PCT/US2015/010797, dated Apr. 28, 2015.
Mori et al., "Isolation and characterization of griffithsin, a novel HIV-inactivating protein, from the reg alga *Griffithsia* sp, " *J. Biol. Chem.*, 280 (10), 9345-9353 (2005).
Ramessar et al., "Can microbicides turn the tide against HIV?," *Curr. Pharm. Des.*, 16 (4), 468-485 (2010).
Ramessar et al., "Isolation and characterization of a novel class of potent anti-HIV proteins from an Australian soft coral (975.6)," *The Faseb Journal*, 28(1), 975.6 (2014).

(Continued)

*Primary Examiner* — Jeffrey S Parkin
(74) *Attorney, Agent, or Firm* — Leydig, Voit & Mayer, Ltd.

(57) ABSTRACT

An isolated and purified nucleic acid molecule that encodes a polypeptide comprising at least eight contiguous amino acids of SEQ ID NO: 1, 2, or 3, wherein the at least eight contiguous amino acids have anti-viral activity, as well as an isolated and purified nucleic acid molecule that encodes a polypeptide comprising at least eight contiguous amino acids of SEQ ID NO: 1, 2, or 3, wherein the at least eight contiguous amino acids have anti-viral activity, a vector comprising such an isolated and purified nucleic acid molecule, a host cell comprising the nucleic acid molecule, optionally in the form of a vector, a method of producing an antiviral polypeptide or conjugate thereof, the anti-viral polypeptide itself, a conjugate or fusion protein comprising the anti-viral polypeptide, and compositions comprising an effective amount of the anti-viral polypeptide or conjugate or fusion protein thereof. Further provided are methods of inhibiting prophylactically or therapeutically a viral infection of a host.

11 Claims, 10 Drawing Sheets

Figure 2:
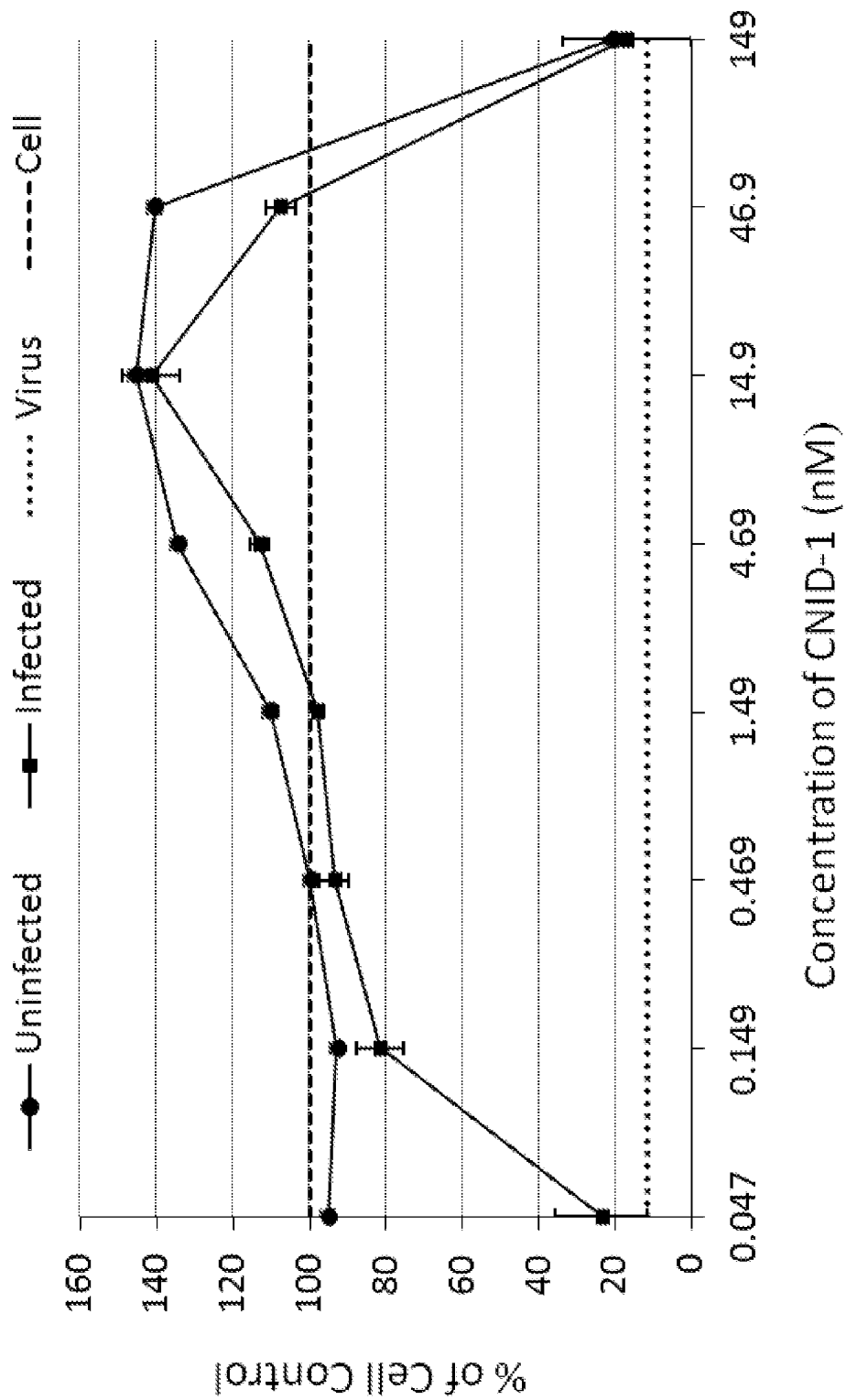
Figure 3:
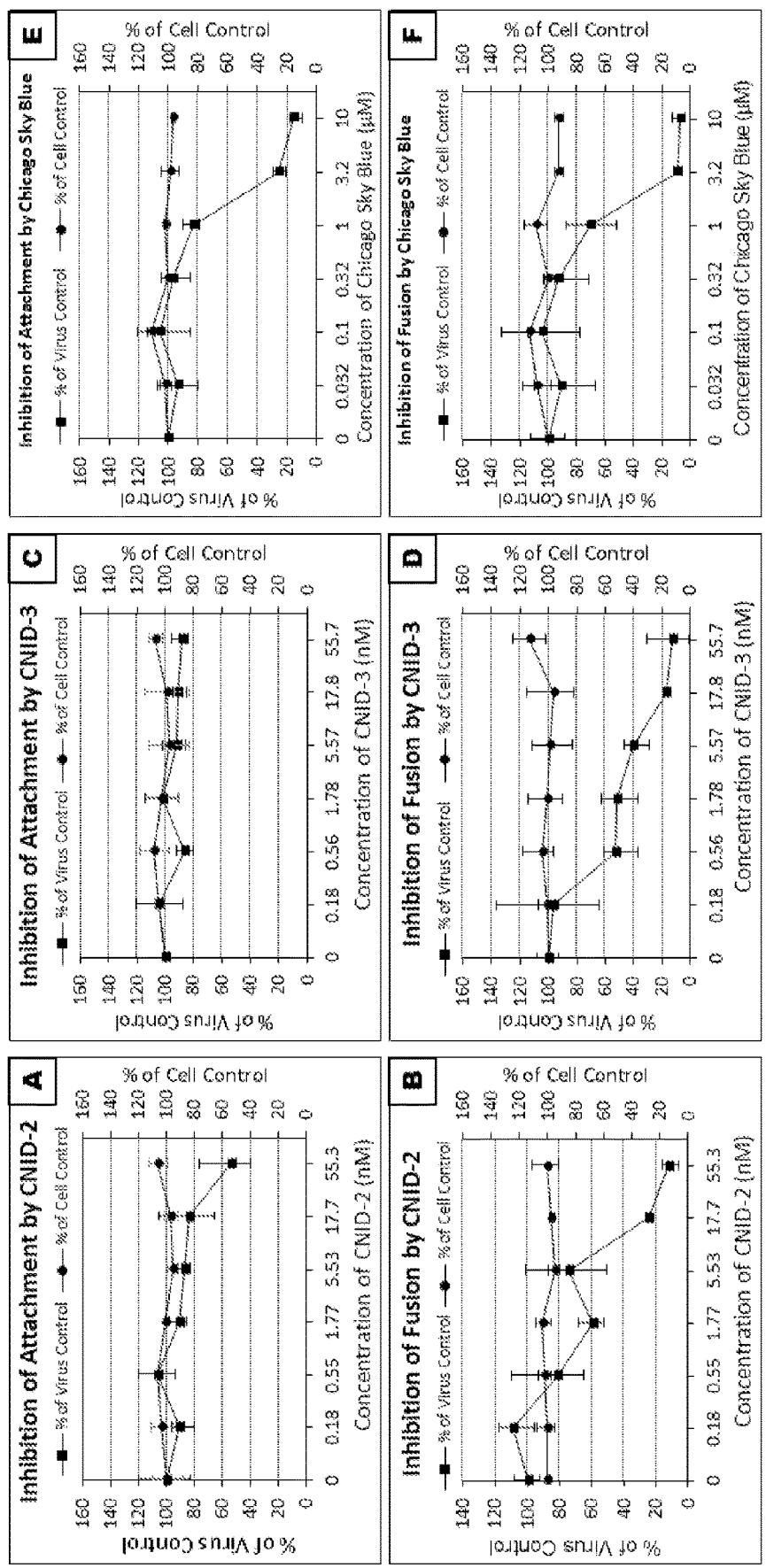

Specification includes a Sequence Listing.

(56) References Cited

OTHER PUBLICATIONS

Rashid et al., "HIV-inhibitory cembrane derivatives from a Philippines collection of the soft coral *Lobophytum* species,"*J. Nat. Prod.*, 63(4), 531-533 (2000).
Rocha et al., "Cnidarians as a source of new marine bioactive compounds—an overview of the last decade and future steps for bioprospecting," *Mar. Drugs*, 9(10), 1860-1886 (2011).
UniProt Accession No. H7ENR6 (dated May 16, 2012).
UniProt Accession No. S5CH60 (dated Oct. 16, 2013).
Wang et al., "New cytotoxic cembranolides from the soft coral *Lobophytum michaelae*," *Mar. Drugs*, 10 (2), 306-318 (2012).
Written Opinion of the International Searching Authority, Application No. PCT/US2015/010797, dated Apr. 28, 2015.
Ziólkowska et al., "Structural studies of algal lectins with anti-HIV activity," *Acta Biochim. Pol.*, 53 (4), 617-626 (2006).
Jimenez et al., "Multi-taxa coral reef community structure in relation to habitats in the Baa Atoll Man and Biosphere UNESCO Reserve (Maldives), and implications for its conservation," *Journal of Sea Research*, 72, 77-86 (Apr. 13, 2012).
European Patent Office, Communication pursuant to Article 94(3) EPC, dated Aug. 29, 2017, 5 pages.
Canadian Intellectual Property Office, Office Action dated Feb. 1, 2021 issued in Canadian Application No. 2,935,123, 7 pages.
GenBank Accession No. AGRW01000054.1 (Mar. 21, 2012) 172 pages.
GenBank Accession No. CY096565 (Aug. 8, 2011) 2 pages.
GenBank Accession No. KC485295.1 (Jul. 14, 2013) 7 pages.

\* cited by examiner

```
CNID1 (MeN)  -GRATIGQLKTSTIPPVTFDVPFDGANIPQDVRFTIATVNGGKGALYNAELGESAGHTIV  59
CNID3        -GKSAYPGQITSDVPFVTFDVPFDGVNIPQDVRFTIATVNGGKLALYNAKLGDPANNTIV  59
              *  : :  **  : * **************.*********** :*****:** :***

CNID1  LESDGDHPIPGTFDPKSGRGLDYLPRGLVLFSSHNYVGNMKMYTEPDSDITADFPPGTPF  119
CNID3  LESDGDHPIPGTFDDPKGRGLDYAFGGLLLFSFHNFVGHKKLYREPDSDITADFPPG--L  117
       *************  **.******  .******  *:.**  *  .** **********:

CNID1  GVSSAITGEGSAFQLNTGIDHTGEFEIIPPNTKRNLAGVFDNEIRSVSPTGGK  172
CNID3  GGSSAITGEGSTVQLYTGIDFTGISEIMPVNTKRNFVVAFGNEFKSVSPTGGG  170
       * *********:.** ****.**  .**  ***** *.* ** :*******
```

FIG. 1

FIG. 9

```
          10         20         30         40         50         60
GRATLGQLKT STIPPVTFDV PFDGANIPQD VRFTIATVNG GKGALYNAEL GESAGHTIVL
   DVGLPKT ATIPPVLFQV PADGAYIMQI NEFTIATVNG GKXXXXXNFF GPSIDDSIVL
GKSAYPGQIT SDVPFVTFDV PFDGVNIPQD VRFTIATVNG GKLALYNAKL GDPANNTIVL 70         80         90        100        110        120
ESDGDHPIPG TFDPKSGRGL DYLPRGLVLF SSHNYVGNMK MYTEPDSDIT ADFPPGTPFG
ESNGDHPIQD FAVEMPPNE- DYEPGGLLDF SSHNYVGNMK MYTEAVNDIT AEFPPQTPLG
ESDGDHPIPG TFDDPKGRGL DYAFGGLLLF SFHNFVGHKK LYREPDSDIT ADFPPGLGGS 130        140        150        160        170
VSSAITGEGS APQLNTGIDH TGEFEIIPPN TKRNLAGVFD NEIRSVSPTG GK
VSSAITWEGV XXXLSVGLNH ADPSQIMPPN EKXXXAGVFD NEFRSVSPTG GK
SAITGEGSTV QLYTGIDPTG ISEIMPVNTK RNFVVAFGNE FKSVSPTGGG

CNID-1 (18122 Da) (SEQ ID NO: 1)
CNID-2 (18088 Da) ~~(SEQ ID NO: 3)~~ (SEQ ID NO: 2)
CNID-3 (17963 Da) ~~(SEQ ID NO: 2)~~ (SEQ ID NO: 3)
```

FIG. 10

ANTI-VIRAL CNIDARINS

CROSS-REFERENCE TO RELATED APPLICATIONS

This patent application is the U.S. national phase of PCT/US2015/010797, filed Jan. 9, 2015, which claims the benefit of U.S. Provisional Patent Application No. 61/925,347, filed Jan. 9, 2014, which applications are incorporated by reference.

STATEMENT REGARDING FEDERALLY SPONSORED RESEARCH AND DEVELOPMENT

This invention was made with Government support under project numbers 1ZIABC011471-06 and 1ZIABC011472-06 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,322 Byte ASCII (Text) file named "724448_ST25.TXT," created on Jun. 21, 2016.

BACKGROUND OF THE INVENTION

The human immunodeficiency virus (HIV)/AIDS epidemic remains a global health problem of unprecedented dimensions. According to the latest UN AIDS report, at the end of 2010, an estimated 34 million people globally were living with HIV. The overall growth of the epidemic has stabilized in recent years and, due to the significant increase in people receiving antiretroviral therapy, the number of AIDS-related deaths has declined. However, there are still hurdles in anti-AIDS treatment due to the emergence of resistant viruses, cross-resistance between drugs and long-term toxicity (Tantillo et al., *J. Mol. Biol.*, 243: 369-387 (1994); Lipsky, *Lancet*, 348: 800-803 (1996)).

HIV/AIDS is the also world's leading cause of death in women ages 15-44, and although the proportion of women living with HIV has remained stable at 50% globally, women continue to bear the burden of the epidemic, especially in sub-Saharan Africa where approximately 6 in 10 HIV-infected adults are women. Heterosexual sex remains the primary mode of HIV transmission in sub-Saharan Africa, and a mix of biology and culture renders women more susceptible to HIV infection than men. Therefore, the dynamics of the epidemic demand the development of safe, effective, and acceptable female-controlled methods such as microbicides, to reduce HIV transmission.

Microbicides are products that could reduce the transmission of HIV and other sexually transmitted infections when used topically in the vagina or rectum (AVAC, AIDS Vaccine Advocacy Coalition (2012)). Microbicides can have a variety of formulations, such as gel, foam, cream, sponge, or intravaginal ring. Since microbicides can be applied by woman before and, in some cases, even after sex, they are being touted as a female-controlled prevention method. Microbicides would complement other prevention methods such as behavior change, abstinence, male and female condoms, male circumcision, oral pre-exposure prophylaxis (PrEP) and hopefully, one day, an HIV vaccine.

The development of microbicidal agents has gained significant focus during the past few years and it has been estimated that a single microbicide with 60% effectiveness could prevent millions of HIV infections each year (Watts & Zimmerman, *Lancet*, 359(9313): 1232-1237 (2002)). Microbicide strategies are primarily targeted at developing compounds that will act early in the virus replication cycle: they can directly inactivate virions or target one of the early stages in the replication cycle including attachment, fusion, entry, reverse transcription and/or integration. Examples of microbicide candidates have been reviewed extensively (Buckheit et al., *AIDS Res. Hum. Retroviruses*, 10: 1497-1506 (2010); Ramessar et al., *Curr. Pharm. Des.*, 16(4): 468-485 (2010); Abdool Karim & Baxter, *Best Pract. Res. Clin. Obstet Gynaecol.*, 26(4): 427-439 (2012). Given the disappointing clinical trial results with surfactants, and buffering agents, these candidates have disappeared from the product development pipeline, and most of microbicide candidates in late-stage development are formulated with antiretroviral drugs that inhibit viral replication, such as reverse transcriptase inhibitors formulated in gels (tenofovir) and intravaginal rings (dapivirine).

Candidates in preclinical development (reviewed by Stone & Harrison, Microbicides—Ways Forward. Alliance for Microbicide Development: Silver Spring, Md. USA, (2010)) include peptides and carbohydrate-binding proteins (lectins) with broad-spectrum anti-HIV activity such as cyanovirin-N (Boyd et al., *Agents Chemother.*, 41: 1521-1530 (1997)), griffithsin (Mori et al., *J. Biol. Chem.*, 280: 9345-9353 (2005)), and actinohivin (Chiba et al., *Biochem. Biophys. Res. Commun.*, 282: 595-601 (2001)). In addition, other naturally occurring lectins have been shown to possess anti-HIV activities: plant-derived concanavalin A (Hansen et al., *AIDS,* 3: 635-641 (1989)) and snowdrop lectin (Balzarini et al., *Antimicrob. Agents Chemother.*, 35: 410-416 (1991); and Balzarini et al., *Antimcrob. Agents Chemother.*, 48: 3858-3870 (2004)) among others (reviewed by Balzarini, *Nat. Rev. Microbiol.*, 5(8): 583-597 (2007)), scytovirin (SVN) (Bokesch et al., *Biochemistry,* 42(9): 2578-2584 (2003)), and more recently, the banana lectin BanLec (Swanson et al., *J. Biol. Chem.*, 285(12): 8646-8655 (2010)) and microvirin from cyanobacteria (Huskens et al., *J. Biol. Chem.*, 285(32): 24845-24854 (2010)).

From a prevention perspective, viral entry is one of the most attractive points for intervention in the viral life cycle, since drug activity is independent of intracellular access. Infection of cells by HIV-1 requires fusion of the cellular and viral membranes, which is mediated by viral envelope glycoproteins (gp120 and gp41) and cell surface receptors (CD4 and a chemokine receptor such as CCR-5 or CXCR-4) on the target cells (Chen & Kim, Cell, 93: 681-684 (1998)). To date, the U.S. Food and Drug Administration (FDA, Antiretroviral drugs used in the treatment of HIV infection. (2012)) has approved 35 antiretrovirals (ARVs) for the treatment of HIV-infected patients. Several of these have been put forward as potential preventative agents including reverse transcriptase inhibitors such as tenofovir. The recent FDA approval of once-daily oral TRUVADA™ (Gilead Sciences Inc.) to reduce the risk of HIV-1 infection among uninfected adults, marks another milestone in the battle against HIV and AIDS . TRUVADA™ (fixed-dose combination of two ARTs, emtricitabine and tenofovir disoproxil fumarate) was approved by the FDA in 2004 for use in combination with other ARTs for the treatment of HIV-1 infection in adults and the recent PrEP approval makes it the first agent indicated for uninfected individuals to reduce their risk of acquiring HIV. However, even though promising results have emerged from several PrEP trials, studies have found that oral tenofovir reaches higher levels in rectal tissues than in vaginal tissue (Dumond et al., *AIDS*, 21: 1899-1907 (2007), Patterson et al., *Science Translational Medicine*, 3(12): 112re4 (2011), Hendrix et al., 18th Conference on Opportunistic Infections and Retroviruses, Boston, Mass., USA; Feb. 27-Mar. 22, 2011, Abstract 35LB (2012)), suggesting that vaginal acquisition of HIV may require a stronger barrier to infection than that provided by oral dosing with the ART combination. In addition, there were significantly more pregnancies in women taking TRUVADA™ than placebo, and these pregnant women were removed from the study (FHI, Family Heath International. Final Results of FEM-PrEP HIV-Prevention Study Indicate Great Attention to Adherence Will be Required in PrEP Programs. (2012)). This raises speculation that TRUVADA™ might have unexpected drug interactions with women's contraception and could thus also alter the thickness of the vaginal mucous membrane thereby altering a woman's vulnerability to HIV (Cairns, *HIV Treatment Update*, 206: 14 (2011)).

Though these agents have demonstrated partial efficacy in some Phase II clinical trials, there remain concerns that the use of ARVs for prevention of HIV infection is a strategy that may not be effective in the longer term due to poor compliance and the resulting potential development of resistant virus (Wegner et al., *AIDS*, 14: 1009-1015 (2000); Sethi et al., *Clin. Infect. Dis.*, 37(8): 1112-1118 (2003); and Gandhi et al., *Clin. Infect. Dis.*, 37: 1693-1698 (2003)). Therefore, it is important to identify novel non-ARV anti-HIV microbicide and PrEP agents which could be used to prevent HIV infection.

BRIEF SUMMARY OF THE INVENTION

The invention provides, among other things, a polypeptide comprising at least eight contiguous amino acids of SEQ ID NO: 1, 2, or 3, wherein the at least eight contiguous amino acids have anti-viral activity, optionally as part of a fusion protein or conjugate. Further provided are nucleic acid molecules encoding the polypeptide, vectors comprising the nucleic acid molecule, and a host cell or organism comprising such a vector.

The invention also provides a method of producing an anti-viral polypeptide, which method comprises expressing the nucleic acid molecule, optionally in the form of a vector, in a host cell or organism. Compositions comprising an effective amount of an aforementioned anti-viral polypeptide or polypeptide conjugate are also provided.

The invention further provides a method of inhibiting prophylactically or therapeutically a viral infection of a host, specifically a retroviral infection of a host, such as an infection of a host with a human immunodeficiency virus (HIV), e.g., HIV-1 or HIV-2. The method comprises administering to the host an effective amount of an anti-viral polypeptide or conjugate comprising at least eight contiguous amino acids of SEQ ID NO: 1, 2, or 3, wherein the at least eight contiguous amino acids have anti-viral activity, whereupon the viral infection is inhibited.

Also provided is a method of inhibiting a viral infection of an animal comprising transforming host cells in vivo with a nucleic acid molecule encoding an above-described polypeptide. Even still further provided is a method of inhibiting a viral infection of an animal comprising transforming host cells with a nucleic acid molecule encoding an above-described polypeptide and placing the transformed host cells into or onto the animal.

An antibody that binds the antiviral polypeptide is provided, as is a composition comprising same.

BRIEF DESCRIPTION OF THE SEVERAL VIEWS OF THE DRAWING(S)

FIG. 1 is an alignment of the primary amino acid sequences of CNID-1 (18.122 kDa, pI 4.92, SEQ ID NO: 1) and CNID-3 (17.963 kDa, pI 4.92, SEQ ID NO: 3) showing a 71% identity between them. Identical amino acids (*), conserved substitutions (:), and semi-conserved substitutions (.) between CNID-1 and CNID-3 are indicated.

FIG. 2 is a graph depicting the concentration dependent anti-HIV activity of CNID-1 on HIV-$1_{RF}$ infected (■) and uninfected (●) CEM-SS cells assessed after 6 days in culture. The percent of cell control is indicated on the y-axis and the concentration of CNID-1 (nM) is indicated on the x-axis. The dotted line indicates untreated virus-infected cell controls and the dashed line indicates untreated, uninfected cell controls. Error bars indicate standard deviation of the mean values obtained from triplicate samples.

FIGS. 3A-F are graphs depicting the concentration-dependent effects of CNID-2 (A and B); CNID-3 (C and D) and Chicago Sky Blue (E and F) on viral attachment and fusion to the cell. Points are represented relative to the infected, nondrug-treated control values. Error bars indicate standard deviation of the mean values obtained from triplicate samples.

Figure 4:
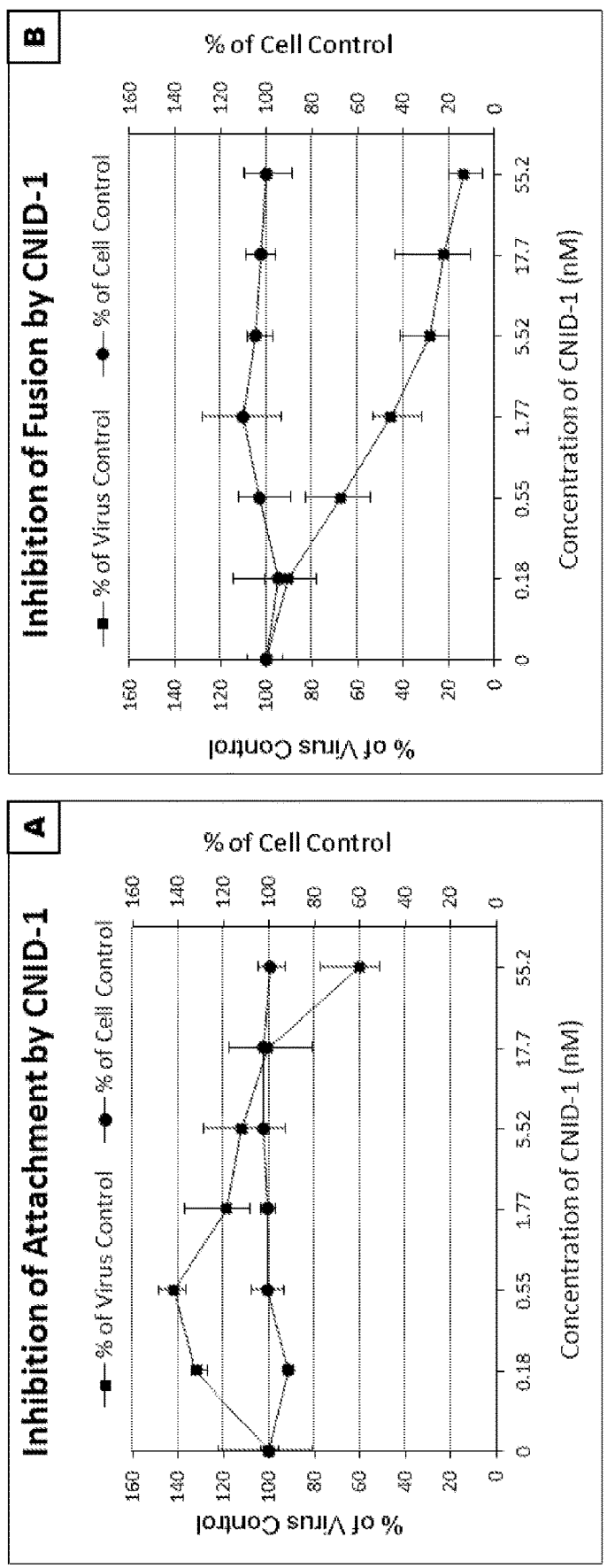

FIGS. 4A-B are graphs depicting the concentration-dependent effects CNID-1 on viral attachment (A) and fusion (B) to the cell. Chicago Sky Blue was used as the control. Points are represented relative to the infected, nondrug-treated control values. Error bars indicate standard deviation of the mean values obtained from triplicate samples.

Figure 5:
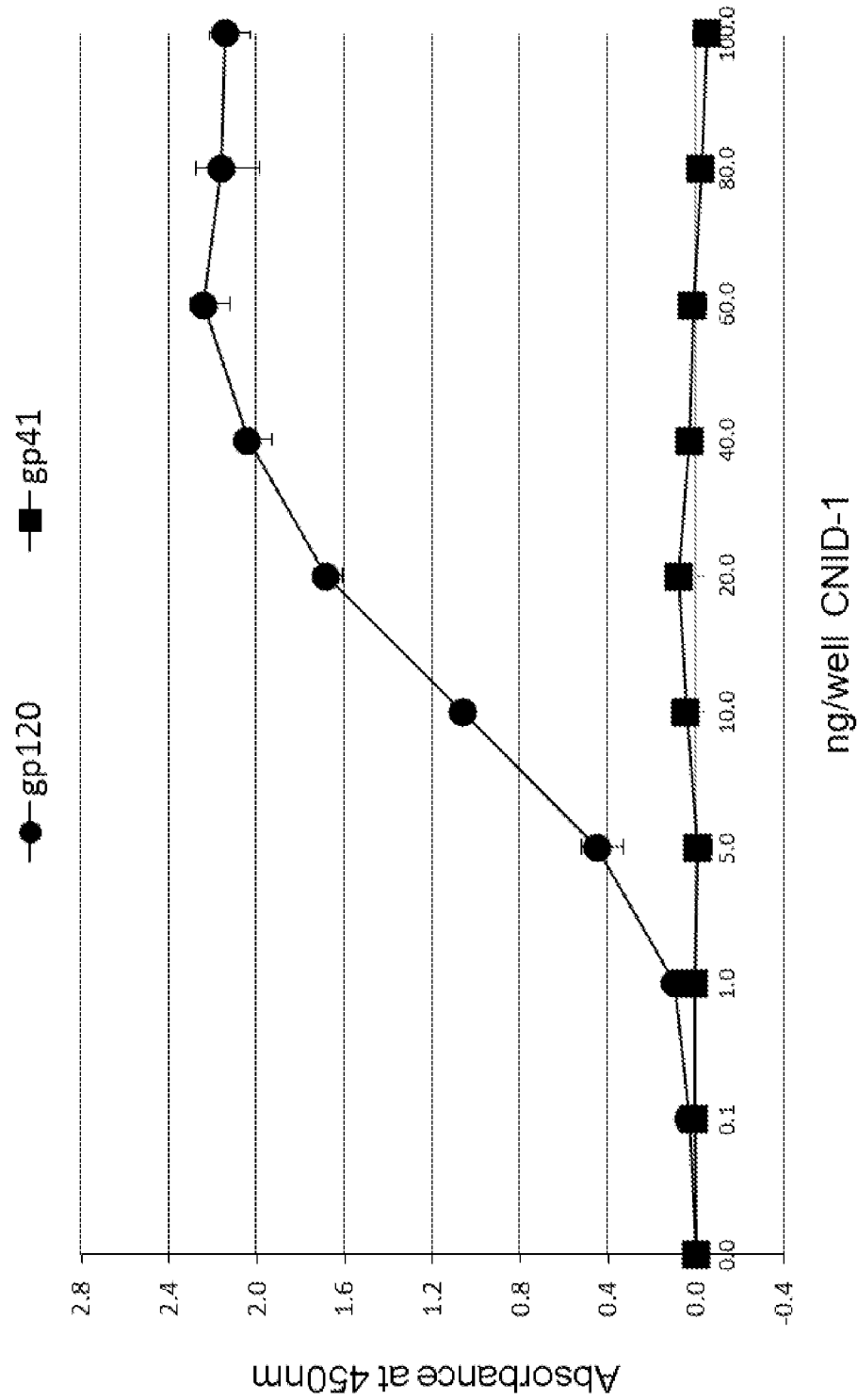

FIG. 5 is a graph depicting the results of an ELISA study of concentration-dependent binding of native CNID-1 to gp120 and gp41. Different serial dilutions of CNID-1 were added to 100 ng/well of native gp120 (■) or gp41 (●). Rabbit anti-CNID-1 polyclonal antibodies were used to detect the bound CNID-1 as indicated by absorbance at 450 nM. Points are averages of triplicate samples (corrected for the blocking agent background values).

Figure 6:
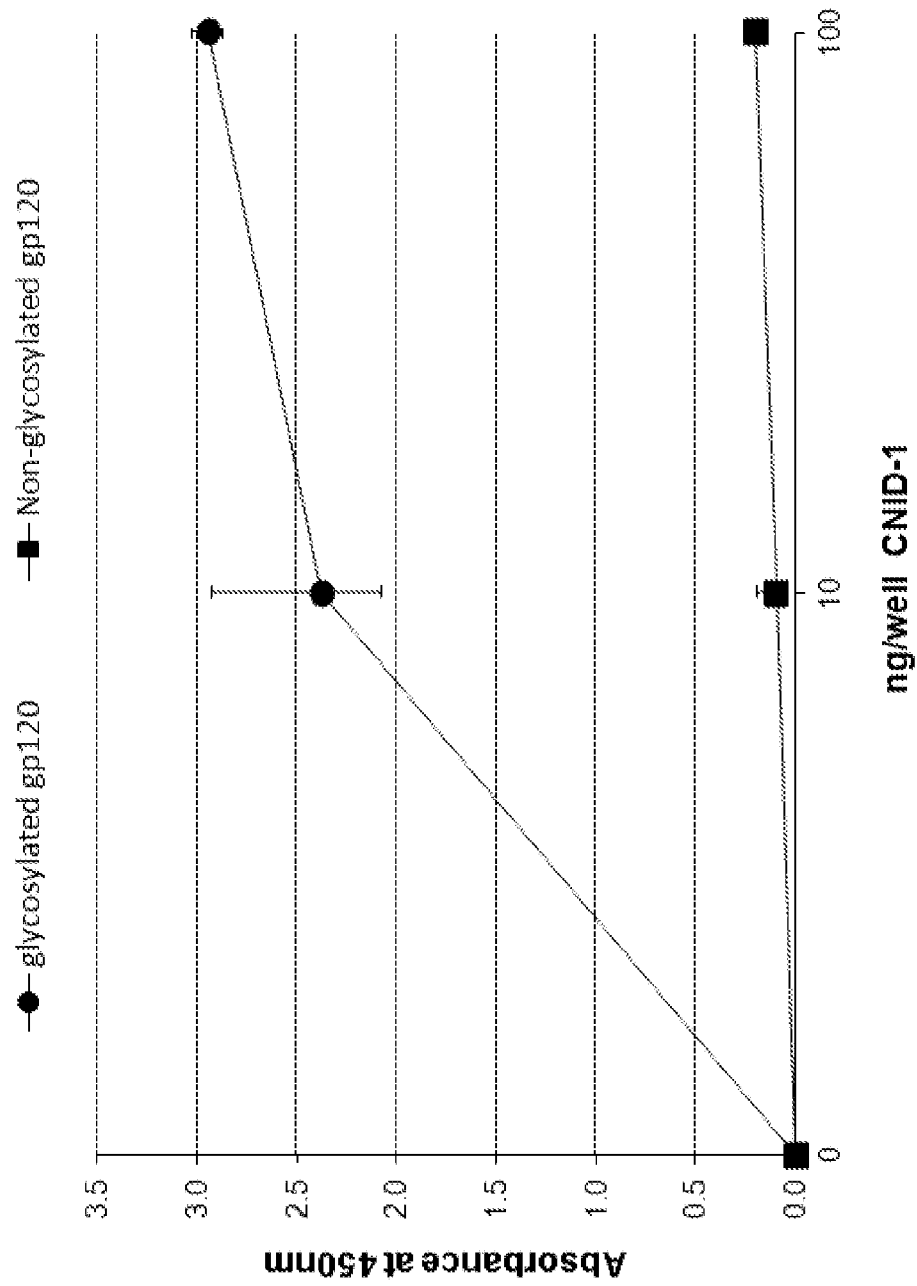

FIG. 6 depicts the results of an ELISA study of concentration-dependent binding of CNID-1 to glycosylated and non-glycosylated gp120. Different serial dilutions of CNID-1 were added to 100 ng/well of glycosylated (●) or nonglycosylated (■) HIV-1 gp120. Rabbit anti-CNID-1 polyclonal antibodies were used to detect the bound rCNID-1 as indicated by absorbance at 450 nM. Points are averages of triplicate samples (corrected for the blocking agent background values).

Figure 7:
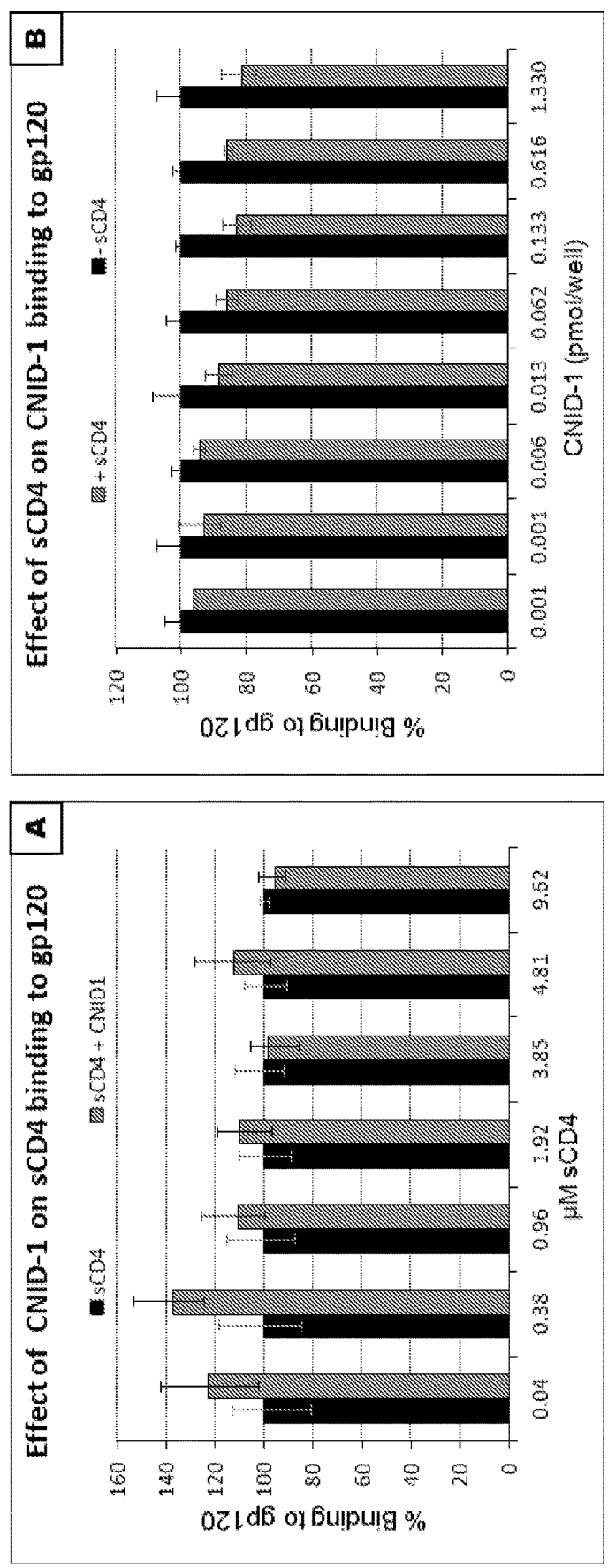

FIGS. 7A-B depict the results of an ELISA study on the effect of (A) pre-treatment of sCD4 on CNID-1 or (B) pre-treatment of CNID-1 on sCD4 binding to gp120. Plate-bound gp120 (100 ng/well) was pre-treated with sCD4 (100 ng/well) or rCNID-1-Trx (250 ng/well) for 60 minutes, before serial dilutions of CNID-1-Trx or sCD4 were added. Rabbit anti-CNID-1 polyclonal antibodies were used to detect the bound rCNID-1-Trx as indicated by absorbance readings. Points are averages of triplicate samples (corrected for the blocking agent background values).

Figure 8:
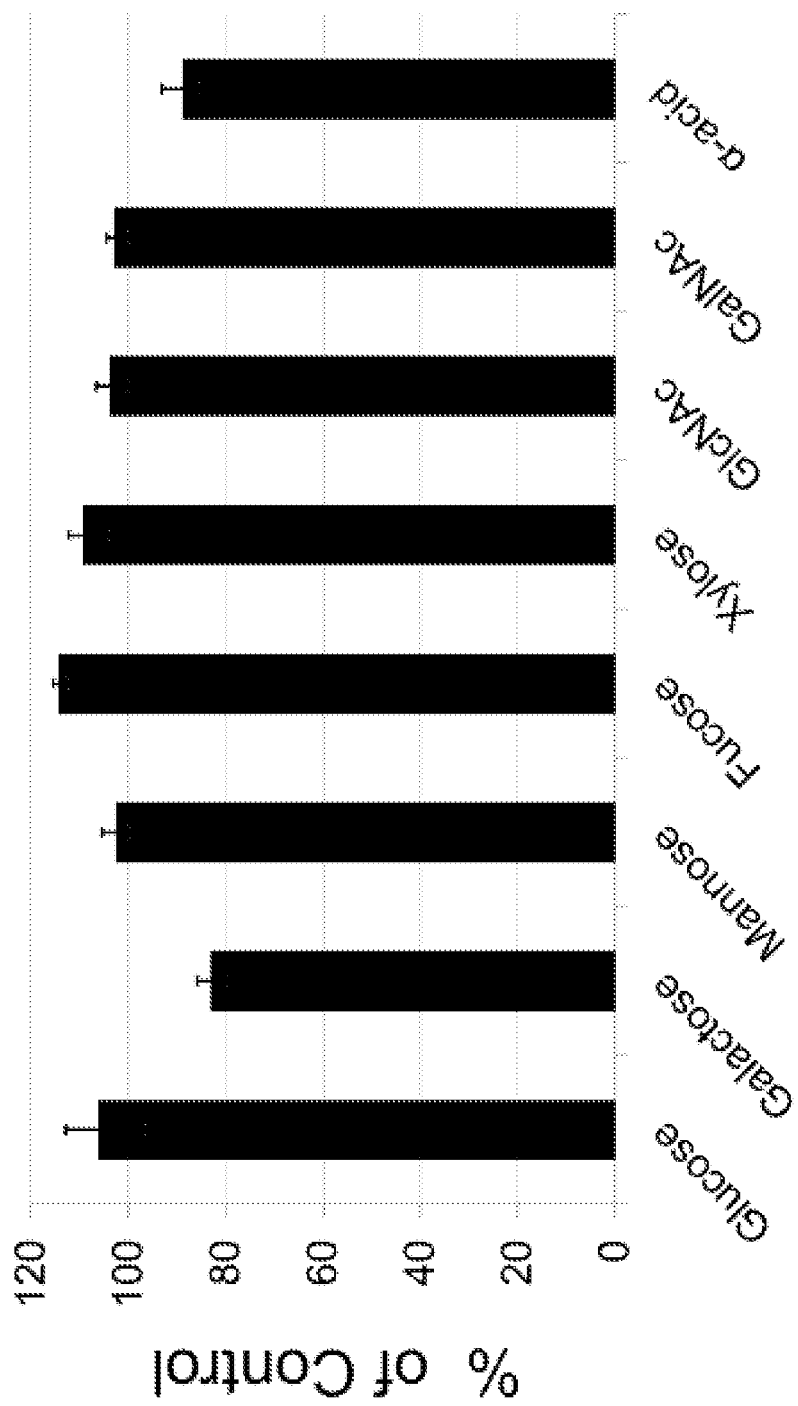

FIG. 8 depicts the results of ELISA study on the influence of monosaccharides on the binding of CNID-1 binding to HIV-1IIIB gp120. 1 mM concentrations of the following sugars were pre-incubated with CNID-1 (100 ng/well) for 5 minutes and added to plate-bound gp120: glucose, galactose, mannose, fucose, xylose, N-acetyl glucosamine (GlcNAc) and N-acetyl galactosamine (GalNAc). Alpha-acid glycoprotein (α-acid) was also tested at 50 ng/well as a carrier of sialic acid bearing oligosaccharide. No significant decrease in CNID-1 binding to gp120 was seen. Bound CNID-1 was visualized with anti-CNID-1 polyclonal antibodies. Points are represented relative to the non-monosaccharide-treated control values. Error bars indicate standard deviation of the mean values obtained from triplicate samples.

FIGS. 9A-D depict the results of an ELISA study on the effect of (A) CV-N on CNID-1 binding to gp120 (B) SVN on CNID-1 binding to gp120, (C) GRFT pretreatment on CNID-1 binding to gp120, and (D) CNID-1 pretreatment on GRFT binding to gp120. Plate-bound gp120 at 100 ng/well, was pre-treated with (●) or without (■) (A) CV-N (100 ng/well), (B) SVN (100 ng/well), (C) GRFT (100 ng/well), or (D) rCNID-1 (500 ng/well) before serial dilutions of rCNID-1 (A, B, C) or GRFT (D) were added. Rabbit anti-CNID-1 or anti-GRFT polyclonal antibodies were used to detect the bound rCNID-1 or GRFT as indicated by absorbance readings. Points are averages of triplicate samples (corrected for the blocking agent background values).

FIG. 10 is an alignment of the primary amino acid sequences of CNID-1 and CNID-3, as well as a partial amino acid sequence of CNID-2. "-" in CNID-2 corresponds to one or more undetermined residues. Spaces were added to arrange the alignments (not based on the exact size of the gap). The N-terminal amino acids of CNID-2 and the length of sequence missing are unknown.

DETAILED DESCRIPTION OF THE INVENTION

The invention provides an anti-viral polypeptide and derivatives thereof, and uses thereof (e.g., medical and research uses), including prophylactic and/or therapeutic applications against viruses. The inventors isolated and identified a novel class of three proteins, called cnidarins (CNID), from an aqueous extract of the soft coral *Synthecium* sp. (phylum Cnidaria) that show low- to sub-nanomolar activity against HIV-1. All three cnidarin proteins (CNID-1, CNID-2 and CNID-3) were shown to inhibit HIV viral fusion but not attachment, indicating a post-CD4 association target is likely responsible for their activity. All three CNID proteins are monomers of approximately 170 amino acids and with molecular weights of ~18 kDa.

CNID-1 and CNID-3 were fully sequenced (see FIGS. 1 and 10). CNID-2 was partially sequenced (see FIG. 10). The CNID proteins show only partial identities (<25%) to translated gene sequences for beta gamma crystalline (from the soft coral *Montipora capitata*), and, in the case of CNID-3, to a hypothetical 135 amino acid protein sequence from fungus *Trichophyton tonsurans* (43% identity to a 51 amino acid fragment of CNID-3).

Accordingly, the invention provides an isolated and purified anti-viral polypeptide of SEQ ID NO: 1, 2, or 3 from *Synthecium* sp. and functional homologs thereof, referred to collectively as "cnidarin." Herein the term "cnidarin" is used generically to refer to a natural cnidarin or any related, functionally equivalent (i.e., anti-viral) polypeptide or derivative thereof. By definition, in this context, a related, functionally equivalent polypeptide or derivative thereof (a) contains a sequence of at least eight contiguous amino acids directly identical to a sub-sequence of eight contiguous amino acids contained within natural cnidarins (e.g., SEQ ID NO: 1, 2, or 3), and (b) can specifically bind to a virus (e.g., HIV), or to an infected host cell expressing one or more viral antigen(s), more specifically an envelope glycoprotein, such as gp120, of the respective virus. In addition, such a functionally equivalent polypeptide or derivative thereof can comprise the amino acid sequence of a natural cnidarin (e.g., SEQ ID NO: 1, 2, or 3), in which 1-60 (e.g., 1-50, 1-40, 1-30 or 1-20), preferably 1-10, more preferably 1, 2, 3, 4, or 5, and most preferably 1 or 2, amino acids have been removed from one or both ends, preferably from only one end, e.g., removed from the C-terminal end (i.e., C-terminal truncation), of natural cnidarin. Alternatively, a functionally equivalent polypeptide or derivative thereof can comprise the amino acid sequence of a native cnidarin (e.g., SEQ ID NO: 1, 2, or 3), in which 1-60 (e.g., 1-50, 1-40, 1-30 or 1-20), preferably 1-10, more preferably 1, 2, 3, 4, or 5, and most preferably 1 or 2, amino acids have been added to one or both ends, preferably from only one end of the native cnidarin.

In one embodiment, the sequence of at least eight contiguous amino acids corresponds to a sequence of SEQ ID NOs: 1, 2 and/or 3 shared by two or more of the cnidarins (see FIGS. 1 and 10). The shared sequence encompasses residues that are identical when two or more of the cnidarins are compared and/or conserved or semi-conserved residues (see FIG. 1).

The term "isolated" as used herein means having been removed from its natural environment. The term "purified" as used herein means having been increased in purity, wherein "purity" is a relative term and not to be construed as absolute purity. By "antiviral" is meant that the polypeptide or fragment thereof can inhibit a virus (e.g., inhibit entry of a virus into a host cell, limit the spread of viral infection by inhibiting cell to cell fusion, and the like), in particular a primate immunodeficiency virus, more specifically a human immunodeficiency virus (HIV), such as HIV-1.

Preferably, the polypeptide or derivative thereof comprises an amino acid sequence that is substantially identical to that of an anti-viral protein from *Synthecium* sp. By "substantially identical" is meant sufficient identity to render the polypeptide or derivative thereof anti-viral, with anti-viral activity characteristic of an anti-viral protein isolated from *Synthecium* sp. At least about 50% identity (e.g., at least about 60% identity, at least about 65% identity, or at least about 70% identity), preferably at least about 75% identity (e.g., at least about 80% identity or at least about 85% identity), and most preferably at least about 90% identity (e.g., at least about 95% identity) should exist.

Alterations of the natural amino acid sequence to produce variant polypeptides can be done by a variety of means known to those skilled in the art. For instance, amino acid substitutions can be conveniently introduced into the polypeptides at the time of synthesis. Alternatively, site-specific mutations can be introduced by ligating into an expression vector a synthesized oligonucleotide comprising the modified site. Alternately, oligonucleotide-directed, site-specific mutagenesis procedures can be used, such as disclosed in Walder et al., *Gene*, 42: 133 (1986); Bauer et al., *Gene*, 37: 73 (1985); Craik, *Biotechniques*, 12-19 (January 1995); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

The ordinarily skilled artisan can generate cnidarin mutants or variants by, for example, substituting or mutating amino acids which are not critical for the anti-viral function of the polypeptide. Ideally, mutations that do not modify the electronic or structural environment of the peptide are generated to retain optimal antiviral activity. For example, amino acid residues which are not responsible for folding or stability of the three-dimensional conformation of the cnidarin polypeptide are candidate residues for mutation.

If desired, the proteins and peptides of the invention (including antiviral fragments, variant polypeptides, fusion proteins, and conjugates) can be modified, for instance, by glycosylation, amidation, carboxylation, or phosphorylation, or by the creation of acid addition salts, amides, esters, in particular C-terminal esters, and N-acyl derivatives of the proteins of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, homologs, variants, and fusion proteins) can be prepared by any of a number of conventional techniques. The polypeptide can be isolated or purified from a naturally occurring source or from a recombinant source. For instance, in the case of recombinant proteins, a DNA fragment encoding a desired polypeptide can be subcloned into an appropriate vector using well-known molecular genetic techniques (see, e.g., Maniatis et al., *Molecular Cloning: A Laboratory Manual,* 2nd ed. (Cold Spring Harbor Laboratory (1989)). The fragment can be transcribed and the polypeptide subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif.; and the like). The polymerase chain reaction optionally can be employed in the manipulation of nucleic acids.

Such polypeptides also can be synthesized using an automated peptide synthesizer in accordance with methods known in the art. Alternately, the polypeptide (and fragments, homologs, variants, and fusion proteins) can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.,* 85: 2149-54 (1963); Barany et al., *Int. J. Peptide Protein Res.,* 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be preformed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, the invention also provides a fusion protein comprising the isolated or purified antiviral polypeptide (or fragment thereof) or variant thereof and one or more other protein(s) having any desired properties or effector functions, such as cytotoxic or immunological properties, or other desired properties, such as to facilitate isolation, purification, analysis, or stability of the fusion protein.

A conjugate comprising a cnidarin polypeptide coupled to at least one effector component, which can be the same or different, is also provided. The effector component can be polyethylene glycol, dextran, albumin, an immunological reagent, a toxin, an antiviral agent, or a solid support matrix. "Immunological reagent" will be used to refer to an antibody, an antibody fragment (e.g., an $F(ab')_2$, an Fab', an Fab, an Fv, an sFv, a dsFv, or an Fc antibody fragment), an immunoglobulin, and an immunological recognition element. An immunological recognition element is an element, such as a peptide, e.g., the FLAG sequence of a recombinant cnidarin-FLAG fusion protein, which facilitates, through immunological recognition, isolation and/or purification and/or analysis of the protein or peptide to which it is attached. An immunological reagent also can be an immunogenic peptide, which can be fused to cnidarin for enhancing an immune response. In this respect, the invention provides an anti-viral conjugate comprising a cnidarin polypeptide or fragment thereof bound to a virus or viral envelope glycoprotein. A cnidarin fusion protein is a type of cnidarin conjugate, wherein a cnidarin is coupled to one or more other protein(s) having any desired properties or effector functions, such as cytotoxic or immunological properties, or other desired properties, such as to facilitate isolation, purification or analysis of the fusion protein or increase the stability or in vivo half-life of the fusion protein. Cnidarin also can be attached to a chemical moiety which allows recognition, isolation, purification, and/or analysis of the protein or peptide. An example of such a chemical moiety is a His tag of a recombinant cnidarin-His fusion protein.

A "toxin" can be, for example, *Pseudomonas* exotoxin. An "antiviral agent" can be AZT, ddI, ddC, 3TC gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, gramicidin, amantatadine, rimantadine, and neuraminidase inhibitors, cyanovirin-N or a functional homolog or derivative thereof (see, for example, U.S. Pat. No. 5,843,882), scytovirin or a functional homolog thereof or derivative thereof (see, for example, WO 03/097814), or griffithsin or a functional homolog thereof or derivative thereof (see, for example, U.S. Pat. No. 7,884, 178).

A "solid support matrix" can be a magnetic bead, a flow-through matrix, a sponge, a stent, a culture plate, or a matrix comprising a contraceptive device, such as a condom, diaphragm, cervical cap, vaginal ring or contraceptive sponge. In an alternative embodiment, a solid support matrix can be an implant for surgical implantation in a host and, if appropriate, later removal.

In view of the foregoing, the invention further provides a composition comprising (i) the isolated or purified antiviral polypeptide (or fragment thereof), a variant thereof, a fusion protein of the antiviral polypeptide (or fragment thereof) or variant thereof, and a conjugate of the antiviral polypeptide (or fragment thereof) or variant thereof, and/or (ii) a carrier, excipient or adjuvant therefor. Preferably, component (i) of the composition is present in an antiviral effective amount and the carrier is pharmaceutically acceptable. By "antiviral effective amount" is meant an amount sufficient to inhibit the infectivity of the virus.

The carrier can be any of those conventionally used and is limited only by chemico-physical considerations, such as solubility and lack of reactivity with the active agent of the invention, and by the route of administration. It is preferred that the pharmaceutically acceptable carrier be one which is chemically inert to the active agent and one which has no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol. The pharmaceutical composition preferably does not comprise mannose or N-acetyl-glucosamine, as these molecules may interfere with the functioning of the antiviral agent.

The invention also provides a method of obtaining a cnidarin from *Synthecium* sp. (see Example 2). Such a method can comprise one or more of (a) identifying an extract of *Synthecium* sp. containing anti-viral activity, (b) removing high molecular weight biopolymers from the extract, and (c) purifying the cnidarin by hydrophobic-interaction chromatography. A particular method to obtain a cnidarin is described in Example 1.

Cnidarin (a polypeptide of SEQ ID NO: 1, 2, or 3), which was isolated and purified using the aforementioned method, was subjected to conventional procedures typically used to determine the amino acid sequence of a given pure protein. Thus, the cnidarin was initially sequenced by N-terminal Edman degradation of intact protein and numerous overlapping peptide fragments generated by endoproteinase digestion. These studies indicated that cnidarin from *Synthecium* sp. was comprised of a unique sequence of 172 (CNID-1) or 170 (CNID-3) amino acids having little or no significant homology or identity to previously described proteins or transcription products of known nucleotide sequences. No more than eight contiguous amino acids from cnidarin were found in any amino acid sequences from known proteins, nor were there any known proteins from any source having significant sequence identity with cnidarin.

Accordingly, the invention provides isolated and purified nucleic acid molecules and synthetic nucleic acid molecules, which comprise a coding sequence for a cnidarin, such as an isolated and purified nucleic acid molecule encoding the amino acid sequence of SEQ ID NO: 1, 2, or 3, and a nucleic acid molecule that is substantially homologous or substantially identical to one of the aforementioned nucleic acid molecules. By "substantially homologous" is meant sufficient homology to render the polypeptide or derivative thereof anti-viral, with anti-viral activity characteristic of an anti-viral protein isolated from *Synthecium*. At least about 50% homology or identity (e.g., at least about 60%, at least about 65%, or at least about 70% homology or identity), preferably at least about 75% homology or identity (e.g., at least about 80% or at least about 85% homology or identity), and most preferably at least about 90% homology or identity (e.g., at least about 95%, at least about 96%, at least about 97%, at least about 98%, or at least about 99% homology or identity) should exist.

The inventive nucleic acid molecule preferably comprises a nucleic acid sequence encoding at least eight (preferably at least 10, more preferably at least 20, and most preferably at least 30) contiguous amino acids of the amino acid sequence of SEQ ID NO: 1, SEQ ID NO: 2, or SEQ ID NO: 3. The inventive nucleic acid molecule also comprises a nucleic acid sequence encoding a polypeptide comprising the amino acid sequence of a native cnidarin, in which 1-60 (e.g., 1-50, 1-40, 1-30 or 1-20), preferably 1-10, more preferably 1, 2, 3, 4, or 5, and most preferably 1 or 2, amino acids have been removed from one or both ends, preferably from only one end, e.g., removed from the C-terminal end, of the native cnidarin. Alternatively, the nucleic acid molecule can comprise a nucleic acid sequence encoding a polypeptide comprising the amino acid sequence of a natural cnidarin (e.g., SEQ ID NO: 1, SEQ ID NO: 2, or SEQ ID NO: 3), in which 1-60 (e.g., 1-50, 1-40, 1-30 or 1-20), preferably 1-10, more preferably 1, 2, 3, 4, or 5, and most preferably 1 or 2, amino acids have been added to one or both ends, preferably from only one end of the native cnidarin. Preferably, the isolated and purified nucleic acid molecule encodes a polypeptide comprising at least eight contiguous amino acids of SEQ ID NO: 1, 2, or 3, which desirably have anti-viral activity. Deletions and substitutions of SEQ ID NO: 1, SEQ ID NO; 2, or SEQ ID NO: 3 are within the skill in the art.

Given the present disclosure, it will be apparent to one skilled in the art that a partial cnidarin gene sequence will likely suffice to code for a fully functional, i.e., anti-viral, such as anti-HIV, cnidarin. A minimum essential DNA coding sequence(s) for a functional cnidarin can readily be determined by one skilled in the art, for example, by synthesis and evaluation of sub-sequences comprising the native cnidarin, and by site-directed mutagenesis studies of the DNA sequence encoding cnidarin.

Using an appropriate DNA coding sequence, a recombinant cnidarin can be made by genetic engineering techniques (for general background see, e.g., Nicholl, in *An Introduction to Genetic Engineering*, Cambridge University Press: Cambridge (1994), pp. 1-5 & 127-130; Steinberg et al., in *Recombinant DNA Technology Concepts and Biomedical Applications*, Prentice Hall: Englewood Cliffs, N.J. (1993), pp. 81-124 & 150-162; Sofer in *Introduction to Genetic Engineering*, Butterworth-Heinemann, Stoneham, Mass. (1991), pp. 1-21 & 103-126; Old et al., in *Principles of Gene Manipulation*, Blackwell Scientific Publishers: London (1992), pp. 1-13 & 108-221; and Emtage, in *Delivery Systems for Peptide Drugs*, Davis et al., eds., Plenum Press: New York (1986), pp. 23-33). For example, a *Synthecium* gene or cDNA encoding a cnidarin can be identified and subcloned. The gene or cDNA then can be incorporated into an appropriate expression vector and delivered into an appropriate polypeptide-synthesizing organism (e.g., *E. coli, S. cerevisiae, P. pastoris*, or other bacterial, yeast, insect, plant or mammalian cells), where the gene, under the control of an endogenous or exogenous promoter, can be appropriately transcribed and translated. Alternatively, the expression vector can be administered to a plant or animal, for example, for large-scale production (see, e.g., Fischer et al., *Transgenic Res.*, 9(4-5): 279-299 (2000); Fischer et al., *J. Biol. Regul. Homeost. Agents*, 14: 83-92 (2000); deWilde et al., *Plant Molec. Biol.*, 43: 347-359 (2000); Houdebine, *Transgenic Research*, 9: 305-320 (2000); Brink et al., *Theriogenology*, 53: 139-148 (2000); Pollock et al., *J. Immunol. Methods*, 231: 147-157 (1999); Conrad et al., *Plant Molec. Biol.*, 38: 101-109 (1998); Staub et al., *Nature Biotech.*, 18: 333-338 (2000); McCormick et al., *PNAS USA*, 96: 703-708 (1999); Zeitlin et al., *Nature Biotech.*, 16: 1361-1364 (1998); Tacker et al., *Microbes and Infection*, 1: 777-783 (1999); Tacket et al., *Nature Med.*, 4(5): 607-609 (1998); and *Methods in Biotechnology, Recombinant Proteins from Plants, Production and Isolation of Clinically Useful Compounds*, Cunningham and Porter, eds., Humana Press: Totowa, N.J. (1998)). Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). Subsequently, the recombinantly produced polypeptide can be isolated and purified using standard techniques known in the art (e.g., chromatography, centrifugation, differential solubility, isoelectric focusing, etc.), and assayed for anti-viral activity.

Alternatively, a natural cnidarin can be obtained from *Synthecium* by non-recombinant methods, and sequenced by conventional techniques. The sequence can then be used to synthesize the corresponding DNA, which can be subcloned into an appropriate expression vector and delivered into a polypeptide-producing cell for en mass recombinant production of the desired polypeptide.

In this regard, the invention also provides a vector comprising a DNA sequence, e.g., a *Synthecium* gene sequence for cnidarin, a cDNA encoding a cnidarin, or a synthetic DNA sequence encoding cnidarin. The vector can be targeted to a cell-surface receptor if so desired. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987) and the references cited herein under "EXAMPLES"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid as described above or a portion thereof ligated to a replication system functional in a prokaryotic or eukaryotic host cell. Replication systems can be derived from ColE1, 2 mμ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, adenovirus-based vectors, and poxvirus vectors. Any of these expression constructs can be prepared using standard recombinant DNA techniques described in, e.g., Sambrook et al., *Molecular Cloning: A Laboratory Manual,* $2^{nd}$ edition, Cold Spring Harbor Laboratory Press, Cold Spring Harbor, N.Y. (1989); Ausubel et al., *Current Protocols in Molecular Biology, Greene* Publishing Associates and John Wiley & Sons, New York, N.Y. (1994); Fischer et al., *Transgenic Res.,* 9(4-5): 279-299 (2000); Fischer et al., *J. Biol. Regul. Homeost. Agents,* 14: 83-92 (2000); deWilde et al., *Plant Molec. Biol.,* 43: 347-359 (2000); Houdebine, *Transgenic Research,* 9: 305-320 (2000); Brink et al., *Theriogenology,* 53: 139-148 (2000); Pollock et al., *J. Immunol. Methods,* 231: 147-157 (1999); Conrad et al., *Plant Molec. Biol.,* 38: 101-109 (1998); Staub et al., *Nature Biotech.,* 18: 333-338 (2000); McCormick et al., *PNAS USA,* 96: 703-708 (1999); Zeitlin et al., *Nature Biotech.,* 16: 1361-1364 (1998); Tacker et al., *Microbes and Infection,* 1: 777-783 (1999); and Tacket et al., *Nature Med.,* 4(5): 607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAMneo (Clonetech).

An expression vector can comprise a native or nonnative promoter operably linked to an isolated or purified nucleic acid as described above. The selection of promoters, e.g., strong, weak, inducible, tissue-specific and developmental-specific, is within the skill in the art. Similarly, the combining of a nucleic acid molecule as described above with a promoter is also within the skill in the art.

The DNA, whether isolated and purified or synthetic, or cDNA encoding a cnidarin can encode for either the entire cnidarin or a portion thereof. Where the DNA or cDNA does not comprise the entire coding sequence of the native cnidarin, the DNA or cDNA can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Genes also can be constructed for specific fusion proteins containing a functional cnidarin component plus a fusion component conferring additional desired attribute(s) to the composite protein. For example, a fusion sequence for a toxin or immunological reagent can be added to facilitate purification and analysis of the functional protein.

Genes can be specifically constructed to code for fusion proteins, which contain a cnidarin coupled to an effector protein, such as a toxin or immunological reagent, for specific targeting to a virus or viral-infected cells, e.g., HIV and/or HIV-infected cells. In these instances, the cnidarin moiety serves not only as a neutralizing agent but also as a targeting agent to direct the effector activities of these molecules selectively against a given virus, such as HIV. Thus, for example, a therapeutic agent can be obtained by combining the HIV-targeting function of a functional cnidarin with a toxin aimed at neutralizing infectious virus and/or by destroying cells producing infectious virus, such as HIV. Similarly, a therapeutic agent can be obtained, which combines the viral-targeting function of a cnidarin with the multivalency and effector functions of various immunoglobulin subclasses.

Viral-targeted conjugates can be prepared either by genetic engineering techniques (see, for example, Chaudhary et al. (1988), supra) or by chemical coupling of the targeting component with an effector component. The most feasible or appropriate technique to be used to construct a given cnidarin conjugate or fusion protein will be selected based upon consideration of the characteristics of the particular effector molecule selected for coupling to a cnidarin. For example, with a selected non-proteinaceous effector molecule, chemical coupling, rather than genetic engineering techniques, may be the only feasible option for creating the desired cnidarin conjugate.

Accordingly, the invention also provides nucleic acid molecules encoding cnidarin fusion proteins. Also provided is a vector comprising a nucleic acid sequence encoding a cnidarin fusion protein and a method of obtaining a cnidarin fusion protein by expression of the vector encoding a cnidarin fusion protein in a protein-synthesizing organism as described above. Accordingly, cnidarin fusion proteins are also provided.

In view of the above, the invention further provides an isolated and purified nucleic acid molecule, which comprises a cnidarin coding sequence, such as one of the aforementioned nucleic acids, namely a nucleic acid molecule encoding an amino acid sequence of SEQ ID NO: 1, SEQ ID NO: 2, or SEQ ID NO: 3 coupled to a second nucleic acid encoding an effector protein. The first nucleic acid preferably comprises a nucleic acid sequence encoding at least eight contiguous amino acids of the amino acid sequence of SEQ ID NO: 1, SEQ ID NO: 2, or SEQ ID NO; 3, which encodes a functional cnidarin, and the second nucleic acid preferably encodes an effector protein, such as a toxin or immunological reagent as described herein.

Accordingly, the invention also further provides an isolated and purified fusion protein encoded by a nucleic acid molecule encoding an amino acid sequence of SEQ ID NO: 1, SEQ ID NO: 2, or SEQ ID NO; 3, either one of which is coupled to a second nucleic acid encoding an effector protein. Preferably, the aforementioned nucleic acid molecules encode at least eight contiguous amino acids of the amino acid sequence of SEQ ID NO: 1, SEQ ID NO: 2, or SEQ ID NO: 3, which desirably have anti-viral activity, coupled to an effector molecule, such as a toxin or immunological reagent as described above. Preferably, the effector molecule targets a virus, more preferably HIV, and, most preferably glycoprotein gp120 of HIV.

The coupling can be effected at the DNA level or by chemical coupling as described above. For example, a cnidarin-effector protein conjugate of the invention can be obtained by (a) selecting a desired effector protein or peptide; (b) synthesizing a composite DNA coding sequence comprising a first DNA coding sequence comprising one of the aforementioned nucleic acid sequences, which codes for a functional cnidarin, coupled to a second DNA coding sequence for an effector protein or peptide, e.g., a toxin or immunological reagent; (c) expressing said composite DNA coding sequence in an appropriate protein-synthesizing organism; and (d) purifying the desired fusion protein to substantially pure form. Alternatively, a cnidarin-effector molecule conjugate of the invention can be obtained by (a) selecting a desired effector molecule and a cnidarin or cnidarin fusion protein; (b) chemically coupling the cnidarin or cnidarin fusion protein to the effector molecule; and (c) purifying the desired cnidarin-effector molecule conjugate to substantially pure form.

Conjugates comprising a functional cnidarin (e.g., an anti-viral polypeptide comprising at least eight contiguous amino acids of SEQ ID NO: 1, 2, or 3, wherein the at least eight contiguous amino acids bind to a virus, in particular an infectious virus, such as HIV, in which case the cnidarin binds to gp120 coupled to an anti-cnidarin antibody, a virus, a viral glycoprotein, or at least one effector component, which can be the same or different, such as a toxin, an immunological reagent, an antiviral agent, or other functional reagent, can be designed even more specifically to exploit the unique viral targeting, e.g., gp120-targeting properties, of cnidarin.

Other functional reagents that can be used as effector components in the inventive conjugates can include, for example, polyethylene glycol, dextran, albumin, a solid support matrix, and the like, whose intended effector functions may include one or more of the following: to improve stability of the conjugate; to increase the half-life of the conjugate; to increase resistance of the conjugate to proteolysis; to decrease the immunogenicity of the conjugate; to provide a means to attach or immobilize a functional cnidarin onto a solid support matrix (e.g., see, for example, Harris, in *Poly(Ethylene Glycol) Chemistry: Biotechnical and Biomedical Applications*, Harris, ed., Plenum Press: New York (1992), pp. 1-14). Conjugates furthermore can comprise a functional cnidarin coupled to more than one effector molecule, each of which, optionally, can have different effector functions (e.g., such as a toxin molecule (or an immunological reagent) and a polyethylene glycol (or dextran or albumin) molecule). Diverse applications and uses of functional proteins and peptides, such as in the present instance a functional cnidarin, attached to or immobilized on a solid support matrix, are exemplified more specifically for poly(ethylene glycol) conjugated proteins or peptides in a review by Holmberg et al. (In *Poly(Ethylene Glycol) Chemistry: Biotechnical and Biomedical Applications*, Harris, ed., Plenum Press: New York (1992), pp. 303-324). Preferred examples of solid support matrices include magnetic beads, a flow-through matrix, and a matrix comprising a contraceptive device, such as a condom, a diaphragm, a cervical cap, a vaginal ring or a sponge.

The anti-viral, e.g., anti-HIV, activity of the cnidarins and conjugates thereof of the invention can be further demonstrated in a series of interrelated in vitro anti-viral assays (Gulakowski et al., *J. Virol. Methods,* 33: 87-100 (1991)), which accurately predict for anti-viral activity in humans. These assays measure the ability of compounds to prevent the replication of HIV and/or the cytopathic effects of HIV on human target cells. These measurements directly correlate with the pathogenesis of HIV-induced disease in vivo. The results of the analysis of the anti-viral activity of cnidarins or conjugates, as set forth in, for instance, Examples 3 and 4, predict accurately the anti-viral activity of these products in vivo in humans and, therefore, establish the utility of the invention.

The cnidarins and conjugates thereof of the invention inhibit a virus, specifically a retrovirus, more specifically an immunodeficiency virus, such as the human immunodeficiency virus (HIV), i.e., HIV-1. The cnidarins and conjugates of the invention can be used to inhibit prophylactically and therapeutically other retroviruses as well as other viruses (see, e.g., *Principles of Virology: Molecular Biology, Pathogenesis, and Control,* Flint et al., eds., ASM Press: Washington, D.C. (2000), particularly Chapter 19). Examples of viruses that may be treated in accordance with the invention include, but are not limited to, HIV (e.g., HIV-1 and HIV-2), Type C and Type D retroviruses, HTLV-1, HTLV-2, HIV, FIV, FLV, SIV, MLV, BLV, BIV, severe acute respiratory syndrome (SARS), equine infectious virus, anemia virus, avian sarcoma viruses, such as Rous sarcoma virus (RSV), hepatitis type A, B, C, non-A, and non-B viruses, arboviruses, varicella viruses, human herpes virus (e.g., HHV-6), measles, mumps, filovirus (e.g., Ebola, such as Ebola strains Sudan, Zaire, Cote d'Ivoire, and Reston), rubella viruses, and influenza viral infection (see, e.g., *Fields Virology,* third edition, Fields et al., eds., Lippincott-Raven Publishers: Philadelphia, Pa. (1996), particularly Chapter 45).

Thus, the invention further provides a composition comprising (i) one or more of an above-described purified or isolated nucleic acid or variant thereof, optionally as part of an encoded fusion protein, and (ii) a carrier, excipient or adjuvant. Preferably, (i) is present in an antiviral effective amount and the composition is pharmaceutically acceptable. The composition can further comprise at least one additional active agent, such as an antiviral agent other than a cnidarin (or antiviral fragment, fusion protein or conjugate thereof), in an antiviral effective amount. Suitable antiviral agents include AZT, ddA, ddI, ddC, 3TC gancyclovir, fluorinated dideoxynucleosides, acyclovir, α-interferon, nonnucleoside analog compounds, such as nevirapine (Shih et al., *PNAS,* 88: 9878-9882, (1991)), TIBO derivatives, such as R82913 (White et al., *Antiviral Res.,* 16: 257-266 (1991)), Ro31-8959, BI-RJ-70 (Merigan, *Am. J. Med.,* 90 (Suppl.4A): 8S-17S (1991)), michellamines (Boyd et al., *J. Med. Chem.,* 37: 1740-1745 (1994)) and calanolides (Kashman et al., *J. Med. Chem.,* 35: 2735-2743 (1992)), nonoxynol-9, gossypol and derivatives, gramicidin, Enfurtide (i.e., T20), cyanovirin-N and functional homologs thereof and fragments thereof (Boyd et al., 1997, supra), scytovirin and functional homologs and fragments thereof (e.g., SD-1), griffithsin and function homologs and fragments thereof, actinohivin (Chiba et al., *Biochem. Biophys. Res. Commun.,* 282: 595-601 (2001)), plant-derived concanavalin A (Hansen et al., *AIDS,* 3: 635-641 (1989)), snowdrop lectin (Balzarini et al., *Antimicrob. Agents Chemother.,* 35: 410-416 (1991); and Balzarini et al., *Antimcrob. Agents Chemother.,* 48: 3858-3870 (2004)), the banana lectin BanLec (Swanson et al., *J. Biol. Chem.,* 285(12): 8646-8655 (2010)) and microvirin from cyanobacteria (Huskens et al., *J. Biol. Chem.,* 285(32): 24845-24854 (2010)).

Other exemplary antiviral compounds include protease inhibitors (see R. C. Ogden and C. W. Flexner, eds., *Protease Inhibitors in AIDS Therapy*, Marcel Dekker, NY (2001)), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), and anti-TAT agents. If the composition is to be used to induce an immune response, it comprises an immune response-inducing amount of the inventive agent and can further comprise an immunoadjuvant, such as polyphosphazene polyelectrolyte.

The pharmaceutical composition can contain other pharmaceuticals, such as virucides, immunomodulators, immunostimulants, antibiotics and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis (1992), supra).

An isolated cell comprising an above-described purified or isolated nucleic acid or variant thereof, optionally in the form of a vector, which is optionally targeted to a cell-surface receptor, is also provided. Examples of host cells include, but are not limited to, a human cell, a human cell line, *E. coli, B. subtilis, P. aerugenosa, S. cerevisiae,* and *N. crassa. E. coli,* in particular *E. coli* TB-1, TG-2, DH5α, XL-Blue MRF' (Stratagene), SA2821 and Y1090. Preferably, the cell is a mammalian cell, bacterium, or yeast. A preferred bacterium is *lactobacillus* or other commensal microorganism. The above-described nucleic acid or variant thereof, optionally in the form of a vector, can be introduced into a host cell using such techniques as transfection, electroporation, transduction, micro-injection, transformation, and the like.

Accordingly, the invention provides a method of inhibiting prophylactically or therapeutically a viral infection, in particular an HIV infection, of a host. The method comprises administering to the host an effective amount of an anti-viral polypeptide or anti-viral polypeptide conjugate comprising at least eight contiguous amino acids of SEQ ID NO: 1 or 2, wherein the at least eight contiguous amino acids have anti-viral activity, whereupon the viral infection is inhibited. The anti-viral polypeptide can be derived from a cnidarin obtained from *Synthecium* or recombinantly produced in accordance with the methods described above.

The inventive anti-viral polypeptide or conjugate thereof can be administered to an animal, preferably a primate (e.g., human), rabbit, guinea pig, hamster, dog, cat, bird, cow, pig, horse, lamb, mouse, or rat, in combination with other anti-viral agents to guard against the propagation of antiviral-resistant strains of virus.

Cnidarins and conjugates thereof collectively comprise polypeptides and proteins, and, as such, are particularly susceptible to hydrolysis of amide bonds (e.g., catalyzed by peptidases). There are various ways to alter molecular structure, if necessary, to provide enhanced stability to the cnidarin or conjugate thereof (Wunsch, Biopolymers, 22: 493-505 (1983); and Samanen, in *Polymeric Materials in Medication*, Gebelein et al., eds., Plenum Press: New York (1985) pp. 227-242), which may be essential for preparation and use of pharmaceutical compositions containing cnidarins or conjugates thereof for therapeutic or prophylactic applications against viruses, e.g., HIV. Possible options for useful chemical modifications of a cnidarin or conjugate include, but are not limited to, the following (adapted from Samanen, J. M. (1985) supra): (a) olefin substitution, (b) carbonyl reduction, (c) D-amino acid substitution, (d) N-methyl substitution, (e) C-methyl substitution, (f) C—C'-methylene insertion, (g) dehydro amino acid insertion, (h) retro-inverso modification, (i) N-terminal to C-terminal cyclization, and (j) thiomethylene modification. Cnidarins and conjugates thereof also can be modified by covalent attachment of carbohydrate and polyoxyethylene derivatives, which are expected to enhance stability and resistance to proteolysis (Abuchowski et al., in *Enzymes as Drugs*, Holcenberg et al., eds., John Wiley: New York (1981), pp. 367-378).

Other important general considerations for design of delivery strategy systems and compositions, and for routes of administration, for protein and peptide drugs, such as cnidarins and conjugates thereof (Eppstein, *CRC Crit. Rev. Therapeutic Drug Carrier Systems,* 5: 99-139 (1988); Siddiqui et al., *CRC Crit. Rev. Therapeutic Drug Carrier Systems,* 3: 195-208 (1987); Banga et al., *Int. J. Pharmaceutics,* 48: 15-50 (1988); Sanders, *Eur. J. Drug Metab. Pharmacokinetics,* 15: 95-102 (1990); and Verhoef, *Eur. J. Drug Metab. Pharmacokinetics,* 15: 83-93 (1990)), also apply. The appropriate delivery system for a given cnidarin or conjugate thereof will depend upon its particular nature, the particular clinical application, and the site of drug action. As with any protein or peptide drug, oral delivery of a cnidarin or a conjugate thereof will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given cnidarin or conjugate thereof. A wide variety of absorption-enhancing agents have been investigated and/or applied in combination with protein and peptide drugs for oral delivery and for delivery by other routes (Verhoef (1990), supra; van Hoogdalem, *Pharmac. Ther.,* 44: 407-443 (1989); and Davis, *J. Pharm. Pharmacol,* 44(Suppl. 1): 186-190 (1992)). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the cnidarins and conjugates thereof, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as cnidarins or conjugates, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes*, Swarbrick, ed., Marcell Dekker, Inc.: New York (1984), pp. 1-60, 88-89, 208-211). Microcapsules also can provide a useful way to effect a prolonged delivery of a protein and peptide drug, such as a cnidarin or conjugate thereof, after injection (Maulding, *J. Controlled Release,* 6: 167-176 (1987)).

Given the aforementioned potential complexities of successful oral delivery of a protein or peptide drug, it is fortunate that there are numerous other potential routes of delivery of a protein or peptide drug, such as a cnidarin or conjugate thereof. These routes include topical, subcutaneous, intravenous, intraarterial, intrathecal, intracisternal, buccal, rectal, nasal, pulmonary, transdermal, vaginal, ocular, and the like (Eppstein (1988), supra; Siddiqui et al. (1987), supra; Banga et al. (1988), supra; Sanders (1990), supra; Verhoef (1990), supra; Barry, in *Delivery Systems for Peptide Drugs*, Davis et al., eds., Plenum Press: New York (1986), pp. 265-275; and Patton et al., *Adv. Drug Delivery Rev,* 8: 179-196 (1992)). With any of these routes, or, indeed, with any other route of administration or application, a protein or peptide drug, such as a cnidarin or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al. (1981), supra; Abuchowski et al., *J. Biol. Chem.,* 252: 3578-3581 (1977); Lisi et al., *J. Appl. Biochem,* 4: 19-33 (1982); and Wileman et al., *J. Pharm. Pharmacol,* 38: 264-271 (1986)). Such modifications also can have advantageous effects on stability and half-life both in vivo and ex vivo.

Procedures for covalent attachment of molecules, such as polyethylene glycol, dextran, albumin and the like, to proteins, such as cnidarins or conjugates thereof, are well-known to those skilled in the art, and are extensively documented in the literature (e.g., see Davis et al., in *Peptide and Protein Drug Delivery*, Lee, ed., Marcel Dekker: New York (1991), pp. 831-864).

Other strategies to avoid untoward immune reactions also can include the induction of tolerance by administration initially of only low doses. In any event, it will be apparent from the present disclosure to one skilled in the art that for any particular desired medical application or use of a cnidarin or conjugate thereof, the skilled artisan can select from any of a wide variety of possible compositions, routes of administration, or sites of application, what is advantageous.

Accordingly, the anti-viral cnidarins and conjugates thereof of the invention can be formulated into various compositions for use, for example, either in therapeutic treatment methods for infected individuals, or in prophylactic methods against viral, e.g., HIV virus, infection of uninfected individuals.

The invention also provides a composition, such as a pharmaceutical composition, which comprises an isolated and purified cnidarin, a cnidarin conjugate, a matrix-anchored cnidarin or a matrix-anchored cnidarin conjugate, such as an anti-viral effective amount thereof. The composition can further comprise a carrier, such as a pharmaceutically acceptable carrier. The composition can further comprise at least one additional anti-viral compound other than a cnidairin or conjugate thereof, such as in an anti-viral effective amount of an anti-viral compound. Suitable anti-viral compounds include cyanovirin, scytovirin, griffithsin, AZT, ddI, ddC, gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, neuroamidase inhibitors, amantatadine, rimantadine, enfurtide, and gramicidin. If the composition is to be used to induce an immune response, it comprises an immune response-inducing amount of a cnidarin or conjugate thereof and can further comprise an immunoadjuvant, such as polyphosphazene polyelectrolyte. The cnidarin used in the composition, e.g., pharmaceutical composition, can be isolated and purified from nature or genetically engineered. Similarly, the cnidarin conjugate can be genetically engineered or chemically coupled.

The inventive compositions can be administered to a host, such as a human, so as to inhibit viral infection in a prophylactic or therapeutic method. The compositions of the invention are particularly useful in inhibiting the growth or replication of a virus, such as a retrovirus, in particular an immunodeficiency virus, such as HIV, specifically HIV-1, inhibiting infectivity of the virus, inhibiting the binding of virus to a host cell, and the like. The compositions are useful in the therapeutic or prophylactic treatment of animals, such as humans, who are infected with a virus or who are at risk for viral infection, respectively. The compositions also can be used to treat objects or materials, such as medical equipment, supplies, or fluids, including biological fluids, such as blood, blood products and vaccine formulations, cells, tissues and organs, to remove or inactivate virus in an effort to prevent or treat viral infection of an animal, such as a human. Such compositions also are useful to prevent sexual transmission of viral infections, e.g., HIV, which is the primary way in which the world's AIDS cases are contracted (Merlon (1993), supra). Adherence of the inventive anti-viral polypeptide or conjugate thereof to a solid support, such as a filter, can be used in clinics to remove all or part of the viral content of a biological solution. For example, filters comprising the inventive anti-viral agents can be used to treat blood supplies prior to transfusion to reduce the risk of viral transmission. Such filters would find particular utility in clinics wherein risk of viral infection is high. It will be appreciated that total removal of the viral content of a biological solution is not required to achieve a beneficial effect. Removal of even a fraction of virus from a biological solution decreases the risk of infection of a patient.

Potential antiviral agents/virucides used or being considered for use against sexual transmission of HIV include, for example, nucleoside reverse transcriptase inhibitors (NRTIs) such as tenofovir and emtricitabine, non-nucleoside reverse transcriptase inhibitors (NNRTIs) such as UC781 and dapivirine (TMC-120), entry inhibitors targeting viral attachment and fusion, the triazole allosteric CCR5 receptor antagonist Maraviroc (Phizer), analogs of the CCR5 ligand RANTES, such as PSC-RANTES, 5P12-RANTES, and 6P4-RANTES, cyanovirin, griffithsin, monoclonal antibodies such as g120-specific antibodies 2G12 and b12 and the g41-specific antibodies 2F5 and 4E10, polyanions such as cellulose sulfate and carageenan which prevent viral attachment, surfactants such as nonoxynol-9 and SAVVY (C31G) which destabilize membranes, buffering agents such as BufferGel (carbopol 974P) which maintain acidic pH in the vaginal cavity, and polyanion naphthalene sulfate (PRO 2000) (see Fletcher et al., *AIDS,* 20: 1237-1245 (2006); Fletcher et al., *Antimicrob. Agents Chemother.,* 53: 487-495 (2009); Lederman et al., *Science,* 306: 485-487 (2004); Liu et al., *Antimicrob. Agents, Chemother.,* 50: 3250-3259 (2006); O'Keefe et al., *Proc. Natl. Acad. Sci. USA,* 106: 6099-6104 (2009); Van Damme et al., *Lancet,* 360: 971-977 (2002); Peterson et al., *PLoS ONE,* 2: e1312 (2007); Skoler-Karpoff et al., *Lancet,* 372: 1977-1987 (2008); Van Damme et al., *N. Eng., Jr. Med.,* 359: 463-472 (2008); and Abdool et al., *AIDS,* 25(7): 957-66 (2011)). The method of prevention of sexual transmission of viral infection, e.g., HIV infection, in accordance with the invention comprises vaginal, rectal, oral, penile or other topical treatment with an anti-viral effective amount of a cnidarin and/or cnidarin conjugate, alone or in combination with another anti-viral agent/virucide as described herein.

Within the context of the present disclosure, it will be appreciated by one skilled in the art that viable host cells containing a DNA sequence or vector of the invention, and expressing a polypeptide or fusion protein of the invention, can be used directly as the delivery vehicle for a cnidarin or fusion protein thereof to the desired site(s) in vivo. Preferred host cells for such delivery of cnidarins or fusion proteins thereof directly to desired site(s), such as, for example, to a selected body cavity, can comprise bacteria or yeast. More specifically, such host cells can comprise suitably engineered strain(s) of lactobacilli, enterococci, or other common bacteria, such as *E. coli,* normal strains of which are known to commonly populate body cavities. More specifically yet, such host cells can comprise one or more selected nonpathogenic strains of lactobacilli, especially those having high adherence properties to epithelial cells, such as, for example, adherence to vaginal epithelial cells, and suitably transformed using the DNA sequences of the present invention.

In one embodiment, the invention provides a "probiotic" or "biotherapeutic" treatment using specifically engineered strains of microorganisms containing a DNA sequence or vector of the invention, and expressing a polypeptide or fusion protein of the invention, which do not occur in nature. Nonetheless, available teachings concerning selection of optimal microbial strains, in particular bacterial strains, for conventional probiotic or biotherapeutic applications can be employed in the context of the invention. For example, selection of optimal *lactobacillus* strains for genetic engineering, transformation, direct expression of cnidirins or conjugates thereof, and direct probiotic or biotherapeutic applications, to treat or prevent viral (e.g., HIV) infection, can be based upon the same or similar criteria typically used to select normal, endogenous or "nonengineered" bacterial strains for conventional probiotic or biotherapeutic therapy. Recent publications describing the use of lactobacilli treatment include Li et al., *J. Acquir. Immune Defic. Syndr.*, 58(4): 379-384 (2011) (describing protection against HIV in macaques fed yogurt with lactobacilli producing cynaovirin) and Yamamoto et al., *BMC Microbiol.*, 13: 4 (2013) (describing vaginal probiotics for prevention of bacterial vaginosis and HIV).

Accordingly, the method of the invention for the prevention of sexual transmission of viral infection, e.g., HIV infection, comprises vaginal, rectal, oral, penile, or other topical, insertional, or instillational treatment with an anti-viral effective amount of a cnidarin, a cnidarin conjugate or fusion protein, a matrix-anchored cnidarin or conjugate or fusion protein thereof, and/or viable host cells transformed to express a cnidarin or conjugate or fusion protein thereof, alone or in combination with one or more other anti-viral compound (e.g., as described above). However, organisms which produce cnidarin or a fragment, homolog, or conjugate thereof can inhibit viruses other than HIV.

Compositions for use in the prophylactic or therapeutic treatment methods of the invention comprise one or more cnidarin(s) or conjugate(s) or fusion protein(s) thereof, either one of which can be matrix-anchored, and desirably a carrier therefor, such as a pharmaceutically acceptable carrier. Pharmaceutically acceptable carriers are well-known to those who are skilled in the art, as are suitable methods of administration. The choice of carrier will be determined in part by the particular cnidarin or conjugate or fusion protein thereof, as well as by the particular method used to administer the composition.

One skilled in the art will appreciate that various routes of administering a drug are available, and, although more than one route can be used to administer a particular drug, a particular route can provide a more immediate and more effective reaction than another route. For example, the anti-viral agent of the invention can be inhaled. Delivery of the anti-viral agent to a location of initial viral contact, such as the nose or mouth, blocks the onset of infection. The anti-viral agent can be administered via subcutaneous injection. Alternatively, in acute or critical medical situations, the anti-viral agent can be administered intravenously. In many cases of infection, a patient generates an immune response to a virus. However, the effects of the viral infection so severely compromise the health of the patient that an effective immune response is not reached prior to death. Administration of the anti-viral agent can prolong the life of the patient until a patient's natural immune defense clears the virus. Furthermore, one skilled in the art will appreciate that the particular pharmaceutical carrier employed will depend, in part, upon the particular cnidarin or conjugate or fusion protein thereof employed, and the chosen route of administration. Accordingly, there is a wide variety of suitable formulations of the composition of the invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science*, 260: 912-915 (1993)).

The anti-viral agent of the invention (e.g., cnidarin or conjugates thereof), alone or in combination with other anti-viral compounds, can be made into aerosol formulations or microparticulate powder formulations to be administered via inhalation. These aerosol formulations can be placed into pressurized acceptable propellants, such as dichlorodifluoromethane, propane, nitrogen, and the like.

The anti-viral agent of the invention (e.g., cnidarin or conjugates thereof), alone or in combinations with other anti-viral compounds or absorption modulators, can be made into suitable formulations for transdermal application and absorption, such as a patch (Wallace et al. (1993), supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.*, 13: 353-359 (1991)).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live *lactobacillus* cultures genetically engineered to directly produce a cnidarin or conjugate or fusion protein thereof of the present invention, such carriers as are known in the art.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli or live *lactobacillus* cultures genetically engineered to directly produce a cnidarin or conjugate or fusion protein thereof of the present invention, such carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, and a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a cnidarin or cnidarin conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. Preferably, the cnidarin is produced by recombinant DNA technology. The cnidarin conjugate can be produced by recombinant DNA technology or by chemical coupling of a cnidarin with an effector molecule as described above. Similarly, formulations suitable for ex vivo sterilization, inactivation, or removal of virus, such as infectious virus, from a sample, such as blood, blood products, sperm, or other bodily products, such as a fluid, cells, a tissue or an organ, or any other solution, suspension, emulsion, vaccine formulation (such as in the removal of infectious virus), or any other material which can be administered to a patient in a medical procedure, can be selected or adapted as appropriate by one skilled in the art, from any of the aforementioned compositions or formulations. However, suitable formulations for ex vivo sterilization or inactivation or removal of virus from a sample or on an inanimate object are by no means limited to any of the aforementioned formulations or compositions. For example, such formulations or compositions can comprise a functional cnidarin, such as that which is encoded by SEQ ID NO: 1 or 2, or anti-viral fragment thereof, such as a fragment comprising at least eight contiguous amino acids of SEQ ID NO: 1 or 2, wherein the at least eight contiguous amino acids bind to a virus, or a conjugate or fusion protein of either of the foregoing, attached to a solid support matrix, to facilitate contacting or binding infectious virus in a sample or removing infectious virus from a sample as described above, e.g., a bodily product such as a fluid, cells, a tissue or an organ from an organism, in particular a mammal, such as a human, including, for example, blood, a component of blood (e.g., plasma, blood cells, and the like), or sperm. Preferably, the anti-viral polypeptide comprises SEQ ID NO: 1 or 2. Also preferably, the at least eight contiguous amino acids bind gp120 of HIV, in particular infectious HIV. As a more specific example, such a formulation or composition can comprise a functional cnidarin, or conjugate or fusion protein thereof, attached to (e.g., coupled to or immobilized on) a solid support matrix comprising magnetic beads, to facilitate contacting, binding and removal of infectious virus, and to enable magnet-assisted removal of the virus from a sample as described above, e.g., a bodily product such as a fluid, cells, a tissue or an organ, e.g., a component of blood, or sperm. Alternatively, and also preferably, the solid support matrix comprises a contraceptive device, such as a condom, a diaphragm, a cervical cap, a vaginal ring, or a sponge. The anti-viral agent also can be encapsulated or dispersed within a solid matrix, such as a vaginal ring or sponge. Methods for encapsulating biotherapeutics into, for example, biocompatible sustained release devices, are known in the art.

As an even more specific illustration, such a composition (e.g., for ex vivo) can comprise a functional (e.g., gp120-binding, HIV-inactivating) cnidarin, or conjugate or fusion protein thereof, attached to a solid support matrix, such as magnetic beads or a flow-through matrix, by means of an anti-cnidarin antibody or at least one effector component, which can be the same or different, such as polyethylene glycol, albumin, or dextran. The conjugate can further comprise at least one effector component, which can be the same or different, selected from the group consisting of, for example, an immunological reagent and a toxin. A flow-through matrix would comprise, for instance, a configuration similar to an affinity column. The cnidarin can be covalently coupled to a solid support matrix via an anti-cnidarin antibody, described below. Methods of attaching an antibody to a solid support matrix are well-known in the art (see, for example, Harlow and Lane. *Antibodies: A Laboratory Manual*, Cold Springs Harbor Laboratory: Cold Spring Harbor, N.Y. (1988)). Alternatively, the solid support matrix, such as magnetic beads, can be coated with streptavidin, in which case the cnidarin or fragment thereof (which comprises at least eight contiguous amino acids of SEQ ID NO: 1, SEQ ID NO: 2, or SEQ ID NO: 3), or a conjugate or fusion protein of either one, is biotinylated. The at least eight contiguous amino acids of SEQ ID NO: 1, 2, or 3 desirably have anti-viral activity and preferably bind gp120 of HIV, which preferably is infectious. Preferably, the anti-viral polypeptide comprises SEQ ID NO: 1, SEQ ID NO: 2, or SEQ ID NO: 3. Such a composition can be prepared, for example, by biotinylating the cnidarin, or conjugate or fusion protein thereof, and then contacting the biotinylated protein or peptide with a (commercially available) solid support matrix, such as magnetic beads, coated with streptavidin. The use of biotinylation as a means to attach a desired biologically active protein or peptide to a streptavidin-coated support matrix, such as magnetic beads, is well-known in the art.

One skilled in the art will appreciate that a suitable or appropriate formulation can be selected, adapted or developed based upon the particular application at hand.

For ex vivo uses, such as virucidal treatments of inanimate objects or materials, blood or blood products, or tissues, the amount of cnidarin, conjugate thereof, fusion protein thereof, or composition of any of the foregoing, to be employed should be sufficient that any virus or virus-producing cells present will be rendered noninfectious or will be destroyed. For example, for HIV, this would require that the virus and/or the virus-producing cells be exposed to concentrations of cnidarin in the range of 0.1-1000 nM. Similar considerations apply to in vivo applications. Therefore, the designation of "anti-viral effective amount" is used generally to describe the amount of a particular cnidarin, conjugate, fusion protein, or composition thereof required for anti-viral efficacy in any given application.

In view of the above, the invention also provides a method of inhibiting prophylactically or therapeutically a viral infection of a host in which an anti-viral effective amount of an above-described anti-viral polypeptide, conjugate, or fusion protein is administered to the host. Upon administration of the anti-viral effective amount of the anti-viral polypeptide, conjugate, or fusion protein, the viral infection is inhibited.

The invention additionally provides a method of prophylactically or therapeutically inhibiting a viral infection of a host in which an anti-viral effective amount of a composition comprising an isolated and purified anti-viral polypeptide, or anti-viral polypeptide conjugate or fusion protein, either one of which comprises at least eight contiguous amino acids of SEQ ID NO: 1, 2, or 3 having anti-viral activity, attached to or encapsulated within a solid support matrix is administered to the host. By "therapeutically" is meant that the host already has been infected with the virus. By "prophylactically" is meant that the host has not yet been infected with the virus but is at risk of being infected with the virus. Prophylactic treatment is intended to encompass any degree of inhibition of viral infection, including, but not limited to, complete inhibition, as one of ordinary skill in the art will readily appreciate that any degree in inhibition of viral infection is advantageous. Preferably, the inventive active agent is administered before viral infection or immediately upon determination of viral infection and is continuously administered until the virus is undetectable. The method optionally further comprises the prior, simultaneous or subsequent administration, by the same route or a different route, of an antiviral agent or another agent that is efficacious in inhibiting the viral infection. Upon administration of the anti-viral effective amount of the composition, the viral infection is inhibited. Preferably, the solid support matrix is a contraceptive device, such as a condom, diaphragm, cervical cap, vaginal ring, or sponge. In an alternative embodiment, a solid support matrix can be surgically implanted and later removed.

For in vivo uses, the dose of a cnidarin, or conjugate or composition thereof, administered to an animal, particularly a human, in the context of the invention should be sufficient to effect a prophylactic or therapeutic response in the individual over a reasonable time frame. The dose used to achieve a desired anti-viral concentration in vivo (e.g., 0.1-1000 nM) will be determined by the potency of the particular cnidarin or conjugate employed, the severity of the disease state of infected individuals, as well as, in the case of systemic administration, the body weight and age of the infected individual. The size of the dose also will be determined by the existence of any adverse side effects that may accompany the particular cnidarin, or conjugate or composition thereof, employed. It is always desirable, whenever possible, to keep adverse side effects to a minimum.

The invention also provides a method of removing virus, such as infectious virus, from a sample. The method comprises contacting the sample with a composition comprising an isolated and purified anti-viral polypeptide or conjugate or fusion protein thereof, comprising at least eight contiguous amino acids of SEQ ID NO:1, SEQ ID NO: 2, or SEQ ID NO: 3. The at least eight contiguous amino acids desirably have anti-viral activity and bind to the virus and the anti-viral polypeptide (or conjugate or fusion protein of either of the foregoing) is attached to a solid support matrix, such as a magnetic bead. "Attached" is used herein to refer to attachment to (or coupling to) and immobilization in or on a solid support matrix. While any means of attachment can be used, preferably, attachment is by covalent bonds. The method further comprises separating the sample and the composition by any suitable means, whereupon the virus, such as infectious virus, is removed from the sample. Preferably, the anti-viral polypeptide comprises SEQ ID NO: 1, SEQ ID NO: 2, or SEQ ID NO: 3. In one embodiment, the anti-viral polypeptide is conjugated with an anti-cnidarin antibody or at least one effector component, which can be the same or different, selected from polyethylene glycol, dextran and albumin, in which case the anti-viral polypeptide is desirably attached to the solid support matrix through at least one effector component. The anti-viral polypeptide can be further conjugated with at least one effector component, which can be the same or different, selected from the group consisting of an immunological reagent and a toxin. In another embodiment, the solid support matrix is coated with streptavidin and the anti-viral polypeptide is biotinylated. Through biotin, the biotinylated anti-viral polypeptide is attached to the streptavidin-coated solid support matrix. Other types of means, as are known in the art, can be used to attach a functional cnidarin (i.e., an anti-viral polypeptide or conjugate as described above) to a solid support matrix, such as a magnetic bead, in which case contact with a magnet is used to separate the sample and the composition. Similarly, other types of solid support matrices can be used, such as a matrix comprising a porous surface or membrane, over or through which a sample is flowed or percolated, thereby selectively entrapping or removing infectious virus from the sample. The choice of solid support matrix, means of attachment of the functional cnidarin to the solid support matrix, and means of separating the sample and the matrix-anchored cnidarin will depend, in part, on the sample (e.g., fluid vs. tissue) and the virus to be removed. It is expected that the use of a selected coupling molecule can confer certain desired properties to a matrix, comprising a functional cnidarin coupled therewith, that may have particularly advantageous properties in a given situation. Preferably, the sample is blood, a component of blood, sperm, cells, tissue or an organ. Also, preferably the sample is a vaccine formulation, in which case the virus that is removed is infectious, such as HIV, although HIV, in particular infectious HIV, can be removed from other samples in accordance with this method.

For instance, the skilled practitioner might select a poly (ethylene glycol) molecule for attaching a functional cnidarin to a solid support matrix, thereby to provide a matrix-anchored cnidarin, wherein the cnidarin is attached to the matrix by a longer "tether" than would be feasible or possible for other attachment methods, such as biotinylation/streptavidin coupling. A cnidarin coupled by a poly(ethylene glycol) "tether" to a solid support matrix (such as magnetic beads, porous surface or membrane, and the like) can permit optimal exposure of a binding surface, epitope, hydrophobic or electrophilic focus, and/or the like, on a functional cnidarin in a manner that, in a given situation and/or for a particular virus, facilitates the binding and/or inactivation of the virus. A preferred solid support matrix is a magnetic bead such that separation of the sample and the composition is effected by a magnet. In a preferred embodiment of the method, the at least eight contiguous amino acids bind gp120 of HIV and HIV is removed from the sample.

Similarly, other types of solid support matrices can be used, such as a matrix comprising a porous surface or membrane, over or through which a sample is flowed or percolated, thereby selectively inhibiting infectious virus (e.g., HIV) in the sample. The choice of solid support matrix, means of attachment of the functional cnidarin to the solid support matrix, and means of separating the sample and the matrix-anchored cnidarin will depend, in part, on the sample (e.g., fluid vs. tissue) and the virus to be inhibited. It is expected that the use of a selected coupling molecule can confer certain desired properties to a matrix, comprising a functional cnidarin coupled therewith, that may have particularly advantageous properties in a given situation.

The methods described herein also have utility in real time ex vivo inhibition of virus or virus infected cells in a bodily fluid, such as blood, e.g., in the treatment of viral infection, or in the inhibition of virus in blood or a component of blood, e.g., for transfusion, in the inhibition or prevention of viral infection. Such methods also have potential utility in dialysis, such as kidney dialysis, and in inhibiting virus in sperm obtained from a donor for in vitro and in vivo fertilization. The methods also have applicability in the context of tissue and organ transplantations.

In summary, a cnidarin attached to a solid support matrix, such as a magnetic bead, can be used to remove virus, in particular infectious virus, including immunodeficiency virus, such as HIV, e.g., HIV-1 or HIV-2, from a sample, such as a sample comprising both infectious and noninfectious virus. The inventive method also can be used to remove viral glycoprotein presenting cells, e.g., infected cells that have, for example, gp120 on their surfaces, from a sample.

The invention, therefore, further provides a composition comprising naturally-occurring, non-infectious virus, such as a composition produced as described above. The composition can further comprise a carrier, such as a biologically or pharmaceutically acceptable carrier, and an immuno-adjuvant. Preferably, the noninfectious virus is an immunodeficiency virus, such as HIV, e.g., HIV-1 or HIV-2. Alternatively, and also preferably, the noninfectious virus is FIV. A composition comprising only naturally-occurring, non-infectious virus has many applications in research and the prophylactic treatment of a viral infection. In terms of prophylactic treatment of a viral infection, the skilled artisan will appreciate the need to eliminate completely all infectious virus from the composition. If desired, further treatment of the composition comprising non-infectious particles with virus-inactivating chemicals, such as imines or psoralens, and/or pressure or heat inactivation, will further the non-infectious nature of the composition. For example, an immune response-inducing amount of the inventive composition can be administered to an animal at risk for a viral infection in order to induce an immune response. The skilled artisan will appreciate that such a composition is a significant improvement over previously disclosed compositions in that the virus is non-infectious and naturally-occurring. Thus, there is no risk of inadvertent infection, greater doses can be administered in comparison to compositions comprising infectious viral particles, and the subsequent immune response will assuredly be directed to antigens present on naturally-occurring virus. The composition comprising naturally-occurring, non-infectious virus can be administered in any manner appropriate to induce an immune response. Preferably, the virus is administered, for example, intramuscularly, mucosally, intravenously, subcutaneously, or topically. Preferably, the composition comprises naturally-occurring, non-infectious human immunodeficiency virus comprising gp120.

The composition comprising naturally-occurring, non-infectious virus can be combined with various carriers, adjuvants, diluents or other anti-viral therapeutics, if desired. Appropriate carriers include, for example, ovalbumin, albumin, globulins, hemocyanins, and the like. Adjuvants or immuno-adjuvants are incorporated in most cases to stimulate further the immune system. Any physiologically appropriate adjuvant can be used. Suitable adjuvants for inclusion in the inventive composition include, for example, aluminum hydroxide, beryllium sulfate, silica, kaolin, carbon, bacterial endotoxin, saponin, and the like.

Thus, the invention also provides a method of inducing an immune response to a virus in an animal. The method comprises administering to the animal an immune response-inducing amount of a composition comprising naturally-occurring, non-infectious virus as described above.

The appropriate dose of a composition comprising naturally-occurring, non-infectious virus required to induce an immune response to the virus in an animal is dependent on numerous factors, such as size of the animal and immune competency. The amount of composition administered should be sufficient to induce a humoral and/or cellular immune response. The amount of non-infectious virus in a particular composition can be determined using routine methods in the art, such as the Coulter HIV p24 antigen assay (Coulter Corp., Hialeah, Fla.). Any suitable dose of a composition comprising non-infectious virus is appropriate so long as an immune response is induced, desirably without the appearance of harmful side effects to the host. In this regard, compositions comprising from about $10^1$ to about $10^5$ particles, preferably from about $10^2$ to about $10^4$ particles, most preferably about $10^3$ particles, are suitable for inducing an immune response.

One of ordinary skill can determine the effectiveness of the composition to induce an immune response using routine methods known in the art. Cell-mediated response can be determined by employing, for example, a virus antigen-stimulated T-cell proliferation assay. The presence of a humoral immune response can be determined, for instance, with the Enzyme Linked Immunosorbent Assay (ELISA). The skilled artisan will appreciate that there are numerous other suitable assays for evaluating induction of an immune response. To the extent that a dose is inadequate to induce an appropriate immune response, "booster" administrations can subsequently be administered in order to prompt a more effective immune response.

In terms of administration of the inventive anti-viral agents or conjugates thereof, the dosage can be in unit dosage form, such as a tablet or capsule. The term "unit dosage form" as used herein refers to physically discrete units suitable as unitary dosages for human and animal subjects, each unit containing a predetermined quantity of a cnidarin or conjugate thereof, alone or in combination with other anti-viral agents, calculated in an amount sufficient to produce the desired effect in association with a pharmaceutically acceptable diluent, carrier, or vehicle.

The specifications for the unit dosage forms of the invention depend on the particular cnidarin, or conjugate or composition thereof, employed and the effect to be achieved, as well as the pharmacodynamics associated with each cnidarin, or conjugate or composition thereof, in the host. The dose administered should be an "anti-viral effective amount" or an amount necessary to achieve an "effective level" in the individual patient.

Since the "effective level" is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1-1000 nM) desired in the patient that corresponds to a concentration of one or more cnidarin or conjugate thereof, which inhibits a virus, such as HIV, in an assay known to predict for clinical anti-viral activity of chemical compounds and biological agents. The "effective level" for agents of the invention also can vary when the cnidarin, or conjugate or composition thereof, is used in combination with AZT or other known anti-viral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the cnidarin or conjugate thereof is administered, time is allowed for the drug to act, and then a suitable reagent is administered to the individual to inactivate the drug.

The pharmaceutical composition can contain other pharmaceuticals, in conjunction with the cnidarin or conjugate thereof, when used to therapeutically treat a viral infection, such as an HIV infection which results in AIDS. Representative examples of these additional pharmaceuticals include anti-viral compounds, virucides, immunomodulators, immunostimulants, antibiotics and absorption enhancers. Exemplary anti-viral compounds include cyanovirin, scytovirin, griffithsin, AZT, ddI, ddC, gancylclovir, fluorinated dideoxynucleosides, nonnucleoside analog compounds, such as nevirapine (Shih et al., *PNAS*, 88: 9878-9882 (1991)), TIBO derivatives, such as R82913 (White et al., *Anti-viral Res.*, 16: 257-266 (1991)), BI-RJ-70 (Merigan, *Am. J. Med.*, 90 (Suppl.4A): 8S-17S (1991)), michellamines (Boyd et al., *J. Med. Chem.*, 37: 1740-1745 (1994)) and calanolides (Kashman et al., *J. Med. Chem.*, 35: 2735-2743 (1992)), nonoxynol-9, gossypol and derivatives, gramicidin, neuraminidase inhibitors, amantadine, enfurtide, and the like. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids.

Administration of a cnidarin or conjugate or fusion protein thereof with other antiretroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between 0.05 µM to 1.0 µM. A range of about 0.005-0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other anti-viral compound, for example, can be given at the same time as the cnidarin or conjugate thereof or the dosing can be staggered as desired. The two drugs also can be combined in a composition. Doses of each can be less when used in combination than when either is used alone.

It will also be appreciated by one skilled in the art that a DNA sequence of a cnidarin or conjugate thereof of the invention can be inserted ex vivo into mammalian cells previously removed from a given animal, in particular a human, host. Such cells can be employed to express the corresponding cnidarin or conjugate or fusion protein in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al. (1994), supra). It is also possible that, as an alternative to ex vivo insertion of the DNA sequences of the invention, such sequences can be inserted into cells directly in vivo, such as by use of an appropriate viral vector. Such cells transfected in vivo are expected to produce anti-viral amounts of cnidarin or a conjugate or fusion protein thereof directly in vivo.

Given the present disclosure, it will be additionally appreciated that a DNA sequence corresponding to a cnidarin or conjugate thereof can be inserted into suitable nonmammalian host cells, and that such host cells will express therapeutic or prophylactic amounts of a cnidarin or conjugate or fusion protein thereof directly in vivo within a desired body compartment of an animal, in particular a human. In one embodiment of the invention, a method of female-controllable prophylaxis against HIV infection comprises the intravaginal administration and/or establishment of, in a female human, a persistent intravaginal population of lactobacilli that have been transformed with a coding sequence of the invention to produce, over a prolonged time, effective virucidal levels of a cnidarin or conjugate thereof, directly on or within the vaginal and/or cervical and/or uterine mucosa. A composition comprising the inventive anti-viral agent and a solid-support matrix, particularly a contraceptive device, such as a condom, a diaphragm, a cervical cap, a vaginal ring, or a sponge, is encompassed by the invention.

The invention also provides antibodies directed to the polypeptides of the invention. The availability of antibodies to any given protein is highly advantageous, as it provides the basis for a wide variety of qualitative and quantitative analytical methods, separation and purification methods, and other useful applications directed to the subject polypeptides. Accordingly, given the present disclosure and the polypeptides of the invention, it will be readily apparent to one skilled in the art that antibodies, in particular antibodies specifically binding to a polypeptide of the invention, can be prepared using well-established methodologies (e.g., such as the methodologies described in detail by Harlow and Lane, in *Antibodies. A Laboratory Manual*, Cold Spring Harbor Laboratory, Cold Spring Harbor (1988), pp. 1-725). Such antibodies can comprise both polyclonal and monoclonal antibodies. Furthermore, such antibodies can be obtained and employed either in solution-phase or coupled to a desired solid-phase matrix, such as magnetic beads or a flow through matrix. Having in hand such antibodies as provided by the invention, one skilled in the art will further appreciate that such antibodies, in conjunction with well-established procedures (e.g., such as described by Harlow and Lane (1988), supra) comprise useful methods for the detection, quantification, or purification of a cnidarin, conjugate thereof, or host cell transformed to produce a cnidarin or conjugate or fusion protein thereof. Accordingly, the invention further provides a composition comprising an anti-cnidarin antibody bound to the anti-viral agent of the invention, preferably an anti-viral polypeptide comprising at least eight contiguous amino acids of SEQ ID NO: 1 or 2.

The invention provides a method of removing virus from a sample. The method comprises (a) contacting the sample with a composition comprising an isolated and purified anti-viral polypeptide or conjugate or fusion protein thereof, wherein (i) the anti-viral polypeptide comprises at least eight contiguous amino acids of SEQ ID NO: 1, 2, or 3, and (ii) the at least eight contiguous amino acids bind to the virus, and (b) contacting the sample with an anti-cnidarin antibody attached to a solid support matrix, whereupon the anti-cnidarin antibody binds to the anti-viral polypeptide or conjugate or fusion protein thereof to which is bound the virus, and (c) separating the solid support matrix from the sample, whereupon the virus is removed from the sample. Preferably, the anti-viral polypeptide comprises SEQ ID NO: 1, 2, or 3. Desirably, the virus that is removed is infectious, such as HIV. The sample can be blood, a component of blood, sperm, cells, tissue or an organ.

The antibody for use in the aforementioned method is an antibody that binds to a polypeptide comprising at least eight contiguous amino acids of SEQ ID NO: 1, 2, or 3, and, which polypeptide can bind to and inactivate a virus. The antibody can be coupled to the solid support matrix using similar methods and with similar considerations as described above for attaching a cnidarin to a solid support matrix. For example, coupling methods and molecules employed to attach an anti-cnidarin antibody to a solid support matrix, such as magnetic beads or a flow-through matrix, can employ biotin/streptavidin coupling or coupling through molecules, such as polyethylene glycol, albumin or dextran. Also analogously, it can be shown that, after such coupling, the matrix-anchored anti-cnidarin antibody retains its ability to bind to a polypeptide comprising at least eight contiguous amino acids of SEQ ID NO: 1, 2, or 3, which polypeptide can bind to and inactivate a virus.

The inventive cnidarins, conjugates, host cells, antibodies, compositions and methods are further described in the context of the following examples. The following examples further illustrate the invention but, of course, should not be construed as in any way limiting its scope.

Example 1

This example illustrates the materials and methods for Examples 2-6.

*Synthecium* Collection and Classification

The soft coral *Synthecium* sp. (phylum Cnidaria, class Hydrozoa, order Thecata also called Leptothecata, family Syntheciidae) was collected at a depth of 10 m on the northern sides of Cumberland Strait, Wessel Islands, N.T., Australia. Sample collection and identification was done by the Australian Institute of Marine Sciences (AIMS) under contract to the National Cancer Institute (National Institutes of Health). A taxonomic voucher specimen (sample number Q66C4766-V) was deposited at the Smithsonian Institution in Suitland, Md. (U.S.A.).

Extraction and Isolation of CNID-1, -2 and -3

Fresh frozen *Synthecium* sp. was ground in the presence of dry ice and first extracted with water followed by a MeOH:$CH_2Cl_2$ (1:1) solvent. Both the organic and aqueous extracts were tested for anti-HIV protective properties in the NCI primary anti-HIV screen (Weislow et al., *J. Natl. Cancer Inst.* 81: 577-586 (1989)). Only the aqueous extract showed anti-HIV activity and was used for further isolation of cnidarin proteins. The freeze dried aqueous extract (2 g used at a time) was resuspended in 120 ml of distilled, deionized water (dd$H_2O$) before precipitation with ethanol (50% final concentration) at −20° C. overnight. Following centrifugation at 3000 rpm for 40 minutes, the supernatant was dried by rotary evaporation to approximately 4-5 ml and lyophilized. The lyophilized sample (resuspended in dd$H_2O$ to a final 25 mg/ml concentration) was brought to 80% saturation with $(NH)_2SO_4$ and protein precipitation occurred initially on ice for 3 hrs and then at 4° C. overnight. The sample was centrifuged at 3000 rpm for 60 minutes and the pellet was resuspended in a minimal volume of dd$H_2O$ before separation by hydrophobic interaction chromatography on a Poros phenyl ether (PE) column (Boehringer Mannheim GmbH, Germany, 4.6×100 mm, 20 µm) using a BioCad Sprint work station (GE Healthcare). The PE column was pre-equilibrated with starting buffer (50 mM sodium phosphate, 1.5M $(NH)_2SO_4$, pH 7.5) before sample injection. Elution occurred at a flowrate of 5 ml/min with (i) starting buffer over 8 column volumes (CV); (ii) linear gradient of 1.5M to 0M $(NH)_2SO_4$ over 40 CV and (iii) 50 mM sodium phosphate over 10 CV. The eluate was monitored for both conductivity and absorbance (280 nm); fractions were pooled accordingly and filtered through a Millipore Centriprep centrifugal filter unit (10 000 Da molecular mass cutoff) to desalt and concentrate the proteins, before being tested for anti-HIV activity. All protein concentrations were determined by colorimetric assay using the BioRad protein assay system with bovine serum albumin (BSA) as the standard according to Bradford (1976).

N-Terminal Protein Sequencing, Amino Acid Analysis, and Mass Spectrometry

N-terminal amino acid sequencing was performed by sequential Edman degradation on an Applied Biosystems model 494 sequencer according to manufacturer's protocols. Amino acid analysis was carried out using a Beckman model 6300 automated amino acid analyzer according to the manufacturer's protocols. LC-MS was performed on an Agilent model 1100 system using a C3 reversed phase column (Zorbax) eluted with a linear gradient from 0 to 100% acetonitrile in $H_2O$ with 5% (v/v) $CH_3COOH$ in the mobile phase. Peaks corresponding to the individual cnidarin proteins were analyzed by electrospray ionization mass spectrometry to determine the accurate masses of individual purified cnidarin proteins.

Circular Dichroism Experiments (CD)

CD spectra of native CNID-1 were obtained on a JASCO J-815 spectropolarimeter (JASCO, Easton, Md.) scanning from 290 to 190 nm at a rate of 50 nm/min. A 1.0-mm path length optical cell was used and spectra were obtained at room temperature with a 1.0-nm bandwidth, and a typical averaging time of 2 seconds. All spectra were corrected for buffer effects by subtracting the spectra of 50 mM Tris buffer pH 8 from the CNID-1 spectra. The corrected CNID-1 spectrum was normalized and the mean residue ellipticity conversion was performed with the K2d software protocol, to estimate CNID-1's secondary structure.

Chemical and Enzymatic Cleavage of Cnidarin Proteins

Purified CNID-1, CNID-2 and CNID-3 were each subjected to digestion with cyanogen bromide (CNBr) and a variety of endoproteinases (Lys-C, Arg-C, Asp-N and Trypsin, Roche Diagnostics, Manheim, Germany) per the manufacturer's instructions. For each protein, the cleaved peptides were purified by reversed-phase HPLC using a gradient of 0.05% aqueous trifluoroacetic acid (TFA) for 20 minutes and then increasing to 60% acetonitrile in 0.05% aqueous TFA over 100 minutes. The purified peptides were sequenced by automated sequential Edman degradation using the Applied Biosystems model 494 sequencer according to the manufacturer's protocols, and the masses of cleaved peptides were analyzed by LC-MS (ESI). Cleavage with the above endoproteinases provided peptide fragments that sufficiently overlapped to completely sequence CNID-1 and CNID-3, except for CNID-1's N-terminal amino acid which was deduced by LC-MS (ESI).

SDS-PAGE, Isoelectric Focusing and Glycoprotein Detection

Samples were resolved on pre-cast NuPAGE® 10% Bis-Tris polyacrylamide gels in MES SDS running buffer (Life Technologies, Grand Island, N.Y.) under reducing conditions according to the manufacturer's instructions. Pre-stained molecular weight standards (MultiMark® Multi-Colored Standard, Invitrogen Life Technologies, Grand Island, N.Y.) were used. Isoelectric focusing (IEF) was carried out on Novex pH3-10 IEF Pre-Cast gels (Invitrogen Life Technologies, Grand Island, N.Y.) according to the manufacturer's protocol. Isoelectric points (pI) were determined by using standard pI markers (Bio-Rad, Hercules, Calif.). Proteins were visualized by Coomassie Blue staining or Periodate Acid Schiffs (PAS)-based detection kit (Sigma-Aldrich, St. Louis, Mo.) for glycoprotein detection according to the manufacturer's instructions.

Anti-HIV Activity Analysis

A 2,3-bis-[2-methoxy-4-nitro-5-sulfophenyl]-2H-tetrazolium-5-carboxanilide inner salt (XTT)-tetrazolium-based assay was used to determine the anti-HIV activity of CNID-1, -2 and -3 against a T-tropic laboratory strain (HIV-$1_{RF}$) in T-lymphoblastic CEM-SS cells as described previously (Gulakowski et al., *J. Virol. Methods*, 33: 87-100 (1991)). CEM-SS cells were maintained in RPMI 1640 media without phenol red and supplemented with 10% fetal bovine serum (BioWhittaker), 2 mM L-glutamine (BioWhittaker), and 50 µg/ml gentamicin (BioWhittaker) (complete medium). Exponentially growing cells were washed and resuspended in complete medium, and a 50 µl aliquot containing $5 \times 10^3$ cells was added to individual wells of a 96-well round-bottom microtiter plate containing serial dilutions of the respective cnidarin protein in a volume of 100 µl of medium. Stock supernatants of HIV-$1_{RF}$ were diluted in complete medium to yield sufficient cytopathicity (80-90% cell kill in 6 days), and a 50 µl aliquot was added to appropriate wells. Plates were incubated for 6 days at 37° C. and then stained for cellular viability using XTT.

To test the anti-HIV activity of CNID1 against HIV primary isolates in fresh human cells, monocyte-tropic HIV-1 strain Ba-L was obtained from the NIAID AIDS Research and Reference Reagent Program (National Institutes of Health, Bethesda, Md.). The low passage HIV-1 pediatric isolate ROJO was derived as described previously (Buckheit et al., *AIDS Res. Hum. Retroviruses*, 10: 1497-1506 (1994)). Human peripheral blood mononuclear cells (PBMCs) and macrophages were isolated from hepatitis and HIV seronegative donors following Ficoll-Paque centrifugation as described elsewhere (Gartner & Popovic, Techniques in HIV Research, Aldovini, A. and Walker B., eds., pp. 59-63, Stockton Press, New York, 1990). Antiviral assays were carried out with 3-day-old phytohaemagglutinin/interleukin-2 stimulated PBMCs or 6-day-cultured monocyte/macrophages. All antiviral evaluations were performed in triplicate in RPMI 1640 supplemented with 10% fetal bovine serum, L-glutamate (2 mM), penicillin (100 units/ml), and streptomycin (100 µg/ml). HIV-1 replication in PBMC (ROJO) or monocyte macrophage (Ba-L) cultures were determined by measurement of reverse transcriptase activity (Buckheit et al., *Antiviral Res.*, 21: 247-265 (1993)) in the supernatants or p24 antigen expression by ELISA (Coulter, Hialeah, Fla.), respectively. Cell viability by formazan dye reduction was determined in replicated cultures using the CellTiter reagent (Promega, Madison, Wis.).

Antiviral data were reported as concentration of the drug required to (i) inhibit 50% virus production (effective concentration, $EC_{50}$) and (ii) reduce cell viability by 50% (cellular cytotoxicity, $CC_{50}$). The HIV reverse transcriptase inhibitor 3'-Azido-3'-deoxythymidine (AZT) was used as a positive control. All assays were carried out in triplicate for all viruses and cells.

Attachment and fusion assays were performed in HeLa-CD4-LTR-β-galactosidase cell lines as described previously (Gartner & Popovic, (1990), supra) with the following modifications. Following the interaction of HIV-$1_{IIIB}$ with HeLa CD4 LTR β-gal cells, viral attachment to HeLa CD4 LTR β-gal cells was detected as cell-associated p24 antigen following a 1 hour adsorption of virus and vigorous washing for removal of unbound virus. Fusion of HIV-$1_{IIIB}$ with HeLa CD4 LTR β-gal cells was detected by chemiluminescence using a single-step lysis and detection method (Tropix Gal-screen, Bedford, Mass.) and results reported as $EC_{50}$ values. Chicago Sky Blue, a polysulfonic acid dye inhibitor of HIV attachment and fusion, was used as a positive control for all assays (Clanton et al., *J. Acquired Immune Defic. Syndr.*, 5: 771-781 (1992)).

Production of Anti-CNID-1 Polyclonal Antibodies

A New Zealand White rabbit was immunized with 100 µg of CNID-1 in Freund's complete adjuvant. Three follow-up booster injections of 50 µg of CNID-1 in Freund's incomplete adjuvant were administered at 2 week intervals, with 10 ml blood drawn prior to each booster injection. Two weeks after the final booster injection, the rabbit was sacrificed and bled out. The IgG fraction of the immune sera of the rabbit was isolated by protein-A Sepharose affinity chromatography (Invitrogen, Camarillo, Calif.) according to the manufacturer's instructions. Reactivity of the polyclonal antibodies for CNID-1 was demonstrated by immunoblot and ELISA studies with 1:200 to 1:2000 of the rabbit immunoglobulin fractions.

Synthesis and *E. coli* Expression of CNID-1

The deduced amino acid sequence of CNID-1 was back-translated to a DNA sequence using an *E. coli* codon preference table and ligated via NcoI/XhoI restriction sites into the Novagen pET32b(+) Trx fusion vector (CNID-1 with N-terminal thioredoxin, Trx, enterokinase recognition sequences and a hexahistidine-tag). The recombinant vector comprising the sequence for the expression of thioredoxin-hexahistidine-CNID-1 (referred to as recombinant CNID-1, rCNID-1-Trx), was transformed into either *E. coli* BL(21)DE3 or BL21-CodonPlus(DE3)-RIPL strains (Stratagene, La Jolla, Calif.). Transformants were cultured in 800 ml of Luria broth (LB) medium containing 50 µg/ml carbenicillin until the $OD_{600}$ reached 0.5-0.7, then induced with 1M isopropyl-β-D-thiogalactopyranoside (IPTG) for 3 hours at 37° C. (250 rpm), or 1 mM IPTG for 18 hours at 25° C. or 18° C. (250 rpm). Cells were collected by centrifugation (5000 rpm for 10 min) and frozen at −80° C. overnight. Defrosted cells were resuspended in 50 mM sodium phosphate pH7.5 buffer supplemented with 1 mM phenylmethanesulfonyl fluoride (PMSF, Sigma) protease inhibitor and 25 U/ml benzonase nuclease (Novagen), and treated with 200 n/ml chicken egg white lysozyme (Sigma) for 30 min at 4° C. Total soluble protein (supernatant) was recovered by centrifugation at 10000 rpm for 20 min at 4° C., and the insoluble pellet (containing inclusion bodies) was stored at −80° C. until further purification. Recombinant CNID-1-Trx was purified on a TALON Superflow metal affinity resin (Clontech Laboratories, Inc.) according to the manufacturer's instructions. The purified rCNID-1-Trx was digested for 16 h at room temperature with recombinant enterokinase (rEK, Novagen), according to the manufacturer's protocol to provide recombinant CNID-1 (rCNID-1). rCNID-1 was purified by hydrophobic interaction chromatography as previously outlined for native CNID-1 purification, with the exception of a 2.5 ml/min flowrate and a linear gradient of 1.5M to 0M $(NH_4)_2SO_4$ over 75 CV. Purification and refolding of rCNID-1-Trx from inclusion bodies were done with a Protein Refolding Kit (Novagen) according to the manufacturer's recommendations, in the presence and absence of 10 mM $CaCl_2$. All purified proteins were concentrated and washed in Amicon ultracentrifugal filter tubes with a molecular weight cutoff of 3 kDa (Millipore, Billerica, Mass.), and concentrations were determined by colorimetric assay using the BioRad protein assay system with BSA as the standard according to Bradford (*Anal. Biochem.*, 72: 248-254 (1976)). The rCNID-1 and the rCNID-1-Trx proteins were analyzed by SDS-PAGE, mass spectrometry and XTT anti-HIV assays as described above. For ELISA studies, only rCNID-1-Trx was used as described below.

Immunoblotting

Recombinant CNID-1 (in fusion with Trx and rEK cleaved forms of rCNID-1) and recombinant HIV-$1_{IIIB}$ gp120 (Immuno Diagnostics, Woburn, Mass.) controls were resolved on 4-12% Bis-Tris pre-cast SDS-PAGE gels (Life Technologies, Grand Island, N.Y.) and blotted onto polyvinylidine difluoride membranes. Membranes were blocked with 3% BSA for 2 hours. For CNID-1 detection, the membrane was incubated overnight with rabbit anti-CNID-1 (1:2000 dilution). For detection of rCNID-1 binding to gp120, membranes were incubated overnight with 1 μg/ml rgp120, then washed thrice with PBST before being incubated with polyclonal rabbit anti-gp120 (1:1000 dilution) overnight. Membranes were washed three times with PBST and further incubated with goat anti-rabbit (H+L), peroxidase conjugated secondary antibody (Thermo Fisher Scientific Inc., Rockford, Ill.) at a 1:1000 dilution for 1 hr. After washing with PBST, signals were detected on Hyblot CL autoradiography film (Denville Scientific, Metuchen, N.J.) using the SignalFire ECL reagent system (Cell Signaling Technology Inc., Danvers, Mass.) according to the manufacturer's protocol.

ELISA Protocols

All ELISA experiments were done at room temperature.

CNID-1 Binding to Reference Proteins

To determine the affinities of CNID-1 for a series of standard proteins, 100 ng each of recombinant HIV-$1_{IIIIB}$gp120 (rgp120, Immuno Diagnostics, Woburn, Mass.), recombinant HIV-$1_{HXB2}$ gp41 (rgp41, Vybion Inc., Ithaca, N.Y.), sCD4 (sCD4-183, 2-domain, NIH AIDS Research & Reference Reagent Program, Germantown, Md.), bovine IgG, aprotinin, human serum albumin (HAS), α-acid glycoprotein, and BSA (Sigma-Aldrich, St. Louis, Mo.) were bound (overnight) to a high-binding 96-well Greiner plate (VWR, Bridgeport, N.J.). The plates were washed with PBS supplemented with 0.05% Tween 20 (PBST) and blocked with 1% BSA solution for 1 hr. Plates were once again washed with PBST and serial dilutions of Europium (Eu)-labeled rCNID-1-Trx (Perkin Elmer Life and Analytical Sciences, Boston, Mass.) were added (100 μl/well); incubation done at room temperature for 1 hr. The plates were washed three times with PBST and 100 μl/well of Delfia Enhancement Solution (PelkinElmer Life and Analytical Sciences, Boston, Mass.) was added. Plates were incubated at room temperature for 15 minutes before being read at 615 nm with the Wallac Victor$^2$ fluorometer (PerkinElmer Life and Analytical Sciences, Shelton, Conn.)

CNID-1 Binding to HIV Envelope Glycoproteins Gp120 and Gp41

High protein binding Greiner 96-well plates (VWR, Bridgeport, N.J.) were coated with 1 pmol/well of recombinant HIV-$1_{IIIIB}$ gp120 (Immuno Diagnostics, Woburn, Mass.) or recombinant HIV-$1_{HXB2}$ gp41 (Vybion Inc., Ithaca, N.Y.) at 4° C. overnight. The wells were emptied and then blocked with 200 μl/well of 3% non-fat dry milk (Bio-Rad, Hercules, Calif.) blocking solution for 2 hrs. A control plate was incubated with blocking solution only. After washing three times with PBST, 0.5-$\log_{10}$ serial dilutions of rCNID-1-Trx were added to triplicate wells of gp120−, gp41− and the blocking solution control plate, and the plates were incubated for 2 hrs. The plates were washed with PBST and 100 W/well of a 1:250 dilution of polyclonal rabbit anti-CNID-1 antibody was added and allowed to incubate for 1 hr, followed by three washes with PBST. Goat anti-rabbit (H+L), peroxidase conjugated secondary antibody (Thermo Fisher Scientific Inc., Rockford, Ill.) was added to each well (100 μl/well of a 1:1000 dilution) and further incubated for 1 hr, followed by three washes with PBST. The TMB 2-component Microwell peroxidase substrate kit (KPL Inc., Gaithersburg, Md.) was used for peroxidase detection: 100 W/well, incubation for 5-10 min and the reaction was stopped by addition of 0.5M HCl (100 W/well) before reading the absorbance at 450 nm.

Effect of Monosaccharides on CNID-1 Binding to Glycoproteins

Additional ELISA studies were performed to assess the effect of monosaccharides on CNID-1 binding to gp120 and gp41. The plates were prepared with native HIV-$1_{IIB}$ gp120 (Advanced Biotechnologies, Columbia, Md.) or recombinant HIV-$1_{HxB2}$ gp41 (Vybion Inc., Ithaca, N.Y.), and 100 ng/well rCNID-1-Trx was added in the presence or absence of 1 mM concentrations of the following sugars: glucose, mannose, galactose, fucose, xylose, N-acetylglucosamine (GlcNAc), N-acetylgalactosamine (GalNAc), or 100 ng/well α-acid glycoprotein (to act as a carrier for sialic acid). The plates were then washed and visualized using anti-CNID-1 polyclonal antibodies as above.

CNID-1 Binding to Glycosylated or Non-Glycosylated HIV-1 gp120

Glycosylation-dependent binding of CNID-1 to gp120 was examined using an ELISA system as above. Briefly, 100 ng/wells of glycosylated recombinant HIV-$1_{IIB}$ gp120 (Immuno Diagnostics, Woburn, Mass.) or nonglycosylated HIV-1 gp120 (MyBioSource LLC, San Diego, Calif.) was added to the wells of two 96-well plates, and incubated overnight at 4° C. The plates were washed and blocked as previously described. Serial dilutions of rCNID-1-Trx were added (100 W/well); incubation done for 2 hrs. The plates were then washed and visualized using anti-CNID-1 polyclonal antibodies as above.

Effect of sCD4, CV-N, SVN or GRFT on CNID-1 Binding to Glycoproteins

Plates to test the effect of sCD4 on CNID-1 binding to gp120 were prepared with recombinant HIV-$1_{IIB}$ gp120 (Immuno Diagnostics, Woburn, Mass.) at 4° C. overnight (100 ng/well) and blocked as previously described. Serial dilutions of rCNID-1-Trx were added in the presence (test plate) or absence (control plate) of 50 ng/well sCD4 (sCD4-183, 2-domain, NIH AIDS Research & Reference Reagent Program, Germantown, Md.) and incubated for 1 hr. Plates were washed and visualized as above. Plates to test for the effect of CV-N, SVN or GRFT on CNID-1 binding to gp120 were prepared with recombinant HIV-$N_{IIB}$ gp120 (Immuno Diagnostics, Woburn, Mass.) at 4° C. overnight (100 ng/well) and blocked as previously described. CV-N (100 ng/well), SVN (100 ng/well) or GRFT (130 ng/well) were added (PBST was added to control wells) and incubated for 30 minutes, followed by serial dilutions of rCNID-1-Trx and further incubated for 75 minutes. The plates were then washed and visualized using anti-CNID-1 polyclonal antibodies as previously outlined.

Effect of CNID-1 on sCD4 or GRFT Binding to Glycoproteins

Plates were prepared with recombinant HIV-$1_{IIIIB}$ gp120 (Immuno Diagnostics, Woburn, Mass.) at 4° C. overnight (100 ng/well) and blocked as previously described. rCNID-1-Trx were added: 250 ng/well for sCD4 test plate or 500 ng/well for the GRFT test plate, and PBST (50 μl/well) to the control plate; incubation done for 2 hrs. The plates were washed as before and serial dilutions of sCD4 (sCD4-183, 2-domain, NIH AIDS Research & Reference Reagent Program, Germantown, Md.) or GRFT were added; incubated for 1 hr 10 minutes. Plates were washed as before. Primary antibodies were added at 100 μl/well: mouse anti-CD4 (ProSci Inc., Poway, Calif.) at 1:1000 dilution or rabbit anti-GRFT at 1:500 dilution; incubation done for 1 hr. The plates were washed as before and peroxidase conjugated secondary antibodies (Thermo Fisher Scientific Inc., Rockford, Ill.) were added at 100 μl/well: goat anti-mouse (sCD4 plate) or goat anti-rabbit (GRFT plate) at a 1:1000 dilution;

incubation for 1 hr. The plates were then washed and visualized as previously outlined.

Example 2

This example illustrates a method of isolating and purifying CNID-1, CNID-2, and CNID-3 from *Synthecium* sp. and elucidating their amino acid sequences.

In vitro anti-HIV activity ($EC_{50}$ of <0.9 µg/ml) was observed in a crude aqueous extract of the soft coral *Synthecium* sp. (phylum Cnidaria) in a whole-cell assay system for HIV-1-induced cytopathicity. Anti-HIV bioassay-guided fractionation of the extract led to the isolation and purification of a class of three new HIV-inhibitory proteins referred to as cnidarin-1 (CNID-1), cnidarin-2 (CNID-2) and cnidarin-3 (CNID-3) based on their elution profile during purification (i.e. early, middle and late eluting proteins were CNID-1, CNID-2 and CNID-3 respectively). The proteins were purified to homogeneity by the sequential use of ethanol precipitation, ammonium sulphate precipitation and hydrophobic interaction chromatography. The calculated total yields (from 5.68 g of original freeze dried aqueous extract) were 2.0 mg, 1.6 mg and 0.5 mg for CNID-1, CNID-2 and CNID-3 respectively.

The proteins, homogenous by SDS-PAGE, all had molecular weights of approximately 18 kDa, and ESI-MS analysis showed single peaks for each protein, corresponding to exact molecular masses of 18,122 Da for CNID-1, 18,088 Da for CNID-2 and 17,963 Da for CNID-3. The isoelectric points determined by native isoelectric focusing of the proteins, were 4.92, 4.92 and 4.85 for CNID-1, CNID-2 and CNID-3 respectively.

None of the CNID proteins were stained in the PAS staining system for glycoproteins, indicating they were not glycosylated. All cnidarin proteins, when reduced and alkylated with 4-vinylpyridine, showed the same molecular masses by ESI-MS indicating they did not contain any cysteine residues. The calculated secondary structure from CD analysis of CNID-1, indicated that it was high in β-sheet (49%), low in α-helices (4%) and 47% of the protein existed as random coil.

The amino acid sequences of the purified cnidarin proteins were established by N-terminal Edman degradation of the intact protein (CNID-3 only) and by N-terminal sequencing of RP-HPLC purified peptide fragments (all cnidarin proteins) that were cleaved by cyanogen bromide and a variety of endopeptidases (Lys-C, Arg-C, Glu-C and Trp, chosen based on amino acid analysis). CNID-1 was N-terminally blocked (N-terminal amino acid could not be identified by N-terminal sequencing of the intact protein) however, using mass spectrometry, CNID-1's N-terminal amino acid was deduced to be sarcosine (N-methyl glycine, 71 Da mass difference). CNID-2 proved to be more difficult in sequencing and required multiple enzymatic digests (using up the remaining purified protein) and only a partial sequence could be identified.

The peptide fragments sufficiently overlapped to completely sequence CNID-1 (172 amino acids) and CNID-3 (170 amino acids) and the resulting molecular weights were in good agreement with that obtained by ESI-MS analysis. CNID-1 and CNID-3 share a 71% sequence similarity when aligned against each other (FIG. 1) with direct homology of 122 amino acids and having 17 conserved amino acid changes and 9 semi-conserved substitutions.

Sequence similarities between CNID-1 and CNID-3 and known proteins or translation products of known nucleotide sequences were searched and only partial amino acid identities were identified. CNID-1 (172 amino acids) showed an overall 21% homology (36% identity from only 58% CNID-1 sequence coverage) to a predicted 166 amino acid protein sequence of beta gamma crystalline isoform (from the soft coral *Montipora capitata*, noted to be associated with coral bleaching, Genbank accession ABV24985). CNID-3 (170 amino acids) showed an overall 13% homology (43% amino acid similarity on only 30% sequence coverage) to a hypothetical 135 amino acid protein sequence (Genbank accession EGD92815.1) from the fungus *Trichophyton tonsurans*. There was no significant overall sequence homology (>25%) with any reported protein or sequence, making this the first report of these unique protein sequences.

A partial sequence of CNID-2 (18088 Da) also was determined (see FIG. 10). In FIG. 10, undetermined sequence is indicated by "-." Additionally, the N-terminal amino acids of CNID2 and the length of sequence missing is not exactly known.

Example 3

This example illustrates the anti-viral activity of the cnidarins.

Anti-HIV activities of cnidarin proteins were initially examined using the T-tropic laboratory strain (HIV-$1_{RF}$) in CEM-SS cells. All three cnidarin proteins elicited concentration-dependent inhibition of virus-induced cell killing with picomolar $EC_{50}$ values (Table 1). Of the three cnidarin proteins, CNID-1 was the most potent (FIG. 2).

TABLE 1

| | | | | Anti-HIV activities of Cnidarin proteins. | | | | |
|---|---|---|---|---|---|---|---|---|
| | | | CNID-1 (nM) | | CNID-2 (nM) | | CNID-3 (nM) | |
| Virus | Target Cell | Tropism | $^a EC_{50}$ | $CC_{50}$ | $^a EC_{50}$ | $CC_{50}$ | $^a EC_{50}$ | $CC_{50}$ |
| RF | CEM-SS | T | 0.0845 | 112 | 0.495 | >430 | 0.114 | >199 |
| Ba-L | Macrophage | M | 1.05 | 3.56 | 9.67 | 9.67 | 5.68 | 4.62 |
| ROJO | PBMC | T | 3.97 | 144 | 8.51 | 356 | 1.50 | 155 |

$^a$Mean $EC_{50}$ values were determined from concentration-response curves from eight dilutions of the test agent; assays for HIV-$1_{RF}$/CEM-SS employed XTT-tetrazolium; HIV-$1_{ROJO}$ were tested in human PBMC cultures by supernatant reverse transcriptase activity; HIV-$1_{Ba-L}$ was tested in human primary macrophage cultures by p24 ELISA assay. AZT was used as a positive control. All data presented are mean values obtained from triplicate samples.

Direct toxicities to the uninfected control cells were seen at much higher concentrations tested (1325-fold for CNID-1, >896-fold for CNID-2 and >1475-fold for CNID-3 when compared to their $EC_{50}$ values, Table 1). When tested against the T-tropic (ROJO) primary isolate of HIV-1, all three cnidarin proteins displayed low-nanomolar activity (Table 1); CNID-3 was the most potent against the ROJO strain with an $EC_{50}$ of 1.55 nM. When tested against the B-aL (M-tropic) isolate, CNID-1 was the most potent ($EC_{50}$ of 1.05 nM) while CNID-2 and CNID-3 had $EC_{50}$ values 9.67 nM and 5.6 8 nM respectively. Cnidarin proteins however displayed toxicity to the macrophages ($CC_{50}$ values of 3.56, 9.67 and 4.62 nM for CNID-1, -2 and -3 respectively.)

Even though CNID-1, CNID-2, and CNID-3 differed in their anti-HIV inhibitions, all three were remarkably potent at the picomolar to low-nanomolar range to both T-tropic strains of HIV-1, which are on average lower (Bokesch et al., Biochemistry, 42(9): 2578-2584 (2003); Chiba et al., Biochem. Biophys. Res. Commun., 282: 595-601 (2001); O'Keefe et al., FEBS Lett., 431(1): 85-90 (1998)) or comparable (Boyd et al., Antimicrob. Agents Chemother., 41: 1521-1530 (1997)) to activities of other antiviral proteins isolated from natural sources, with the exception of griffithsin (Mori et al., J. Biol. Chem., 280: 9345-9353 (2005)) which has more potent HIV inhibitory activity.

All three cnidarin proteins were further tested for virus binding/attachment and fusion of the virus (HIV-1$_{IIIB}$) to target cells (HeLa CD4 LTR β-galactosidase cells). Interestingly all three cnidarin proteins did not inhibit viral attachment to the cell ($EC_{50}$ values of >55 nm; Table 2). This result is similar to those reported for other anti-HIV proteins such as CV-N, SVN and GRFT (Boyd et al., 1997, supra; Bokesch et al., 2003, supra; Mori et al., 2005, supra).

All three cnidarins did, however, inhibit viral fusion in a concentration dependent manner and thereby subsequent infection of the cell, indicating that CNID-1, CNID-2 and CNID-3 all have functions and act in the post-attachment cascade of HIV infection (FIGS. 3A-F and Table 2).

TABLE 2

Effects of Cnidarin proteins on virus-cell interactions

| Protein | [a]Inhibition of Attachment (nM) | | [a]Inhibition of Fusion (nM) | |
|---|---|---|---|---|
| | $EC_{50}$ | $CC_{50}$ | $EC_{50}$ | $CC_{50}$ |
| CNID-1 | >55.2 | >55.2 | 1.49 | >55.2 |
| CNID-2 | >55.3 | >55.3 | 11.6 | >55.3 |
| CNID-3 | >55.7 | >55.7 | 2.06 | >55.7 |

[a]Chicago Sky Blue, a polysulfonic acid dye inhibitor of HIV attachment and fusion, was used as a positive control.

The $EC_{50}$ values were 1.49, 11.6 and 2.06 nM for CNID-1, CNID-2 and CNID-3 respectively, with CNID-1 being the most potent (Table 2). Although CNID-1 did not inhibit attachment (FIG. 4A), even at a high test concentration of >50 nM, it was the most potent at inhibiting fusion, with an $EC_{50}$ value of 1.49 nM (FIG. 4B).

The cnidarin proteins, therefore, represent a new class of protein fusion inhibitors, similar in mechanism but distinct in chemical composition from those previously reported.

Example 4

This example illustrates cnidarin's ability to bind to HIV envelope glycoproteins.

CNID-1 was tested for its ability to bind HIV envelope glycoproteins gp120 and gp41. CNID-1 had a direct interaction with HIV by its specific binding to viral glycoprotein gp120 in a concentration-dependent manner in ELISA studies (FIG. 5). In particular, CNID-1 specifically bound to gp120-treated microtiter plate wells in a concentration dependent manner (FIG. 5). Immunoblots further confirmed specific binding of rCNID-1-Trx and rEK cleaved rCNID-1 to gp120.

This result is similar to that previously reported for antiviral lectins in the finding that CNID-1 bound to gp120 but not gp41. With CV-N, SVN and GRFT, gp120 binding was significantly favored over gp41 binding (Boyd et al., 1997, supra; Bokesch et al., 2003, supra; Mori et al., 2005, supra).

CNID-1 binding to gp120 appears dependant on glycosylation since it bound better to glycosylated gp120 as compared to non-glycosylated gp120 (FIG. 6). CNID-1 binding to gp120 was not inhibited by a variety of monosaccharides (FIG. 8), supporting that CNID-1 does not require larger carbohydrate structures for efficient binding.

Further studies examined CNID-1 binding to gp120 in the presence or absence of sCD4. ELISA tests showed that pre-treatment with CNID-1 did not block subsequent binding of sCD4 to gp120 (FIG. 7A) and similarly, pretreatment with sCD4 did not block CNID-1 binding to gp120 (FIG. 7B). This indicates that CNID-1 binding to gp120 is distinct from the interaction of CD4 with gp120 and this result is consistent with the viral attachment/fusion assay results that suggest CNID-1's antiviral effects occur after initial virus-to-cell attachment but prior to viral entry/fusion.

Example 5

This example demonstrates the effects of monosaccharides, lectins or sCD4 on cnidarin's binding to gp120.

Further ELISA experiments were conducted using specific monosaccharides (glucose, galactose, mannose, fucose, xylose, GlcNac and GalNAc) which were tested for their ability to inhibit CNID-1 binding to glycosylated gp120. The results show that at 1 mM concentrations, none of the monosaccharides inhibited CNID-1 binding (FIG. 8). CNID-1 binding to gp120 was also not inhibited by the heavily sialylated glycoprotein α-acid glycoprotein (FIG. 8).

Example 6

This example demonstrates the differences between cnidarins and other anti-HIV proteins.

Figure 9:
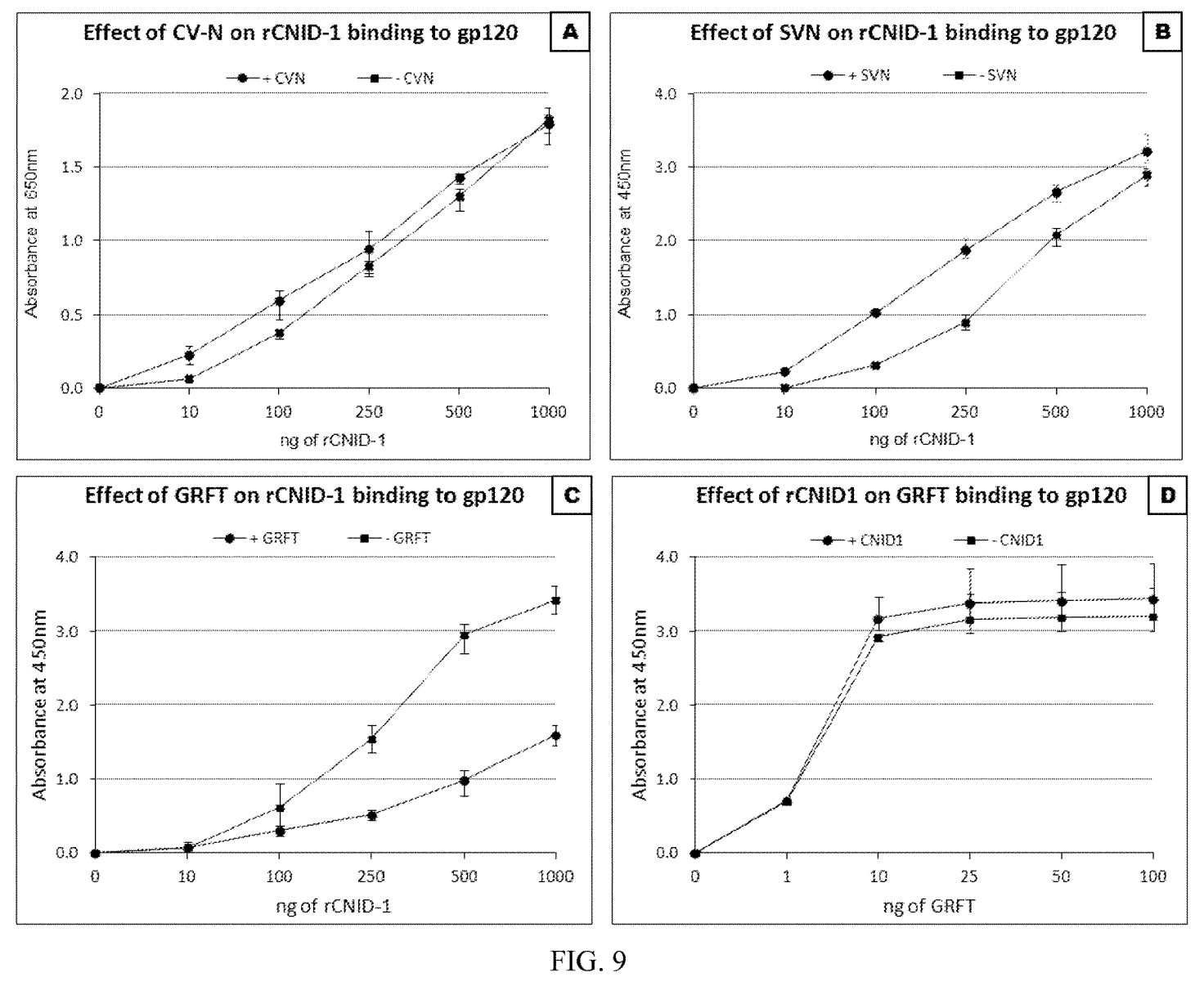

ELISA experiments were performed to assess CNID-1 binding to gp120 pre-treated with CV-N, SVN or GRFT (protein amounts chosen at >80% saturation of binding to gp120). Surprisingly, CV-N and SVN pre-treatment did not affect CNID-1 binding to the viral glycoproteins, and seem to promote slightly better binding of CNID-1 to gp120 (FIG. 9A-B). This data indicates that CNID-1 has a different binding site than CV-N and SVN on gp120 and therefore, potentially a different mechanism of action that these lectins.

Pretreatment of gp120 with GRFT, on the other hand, reduced CNID-1 binding to gp120 (FIG. 9C) but not completely. As GRFT is a monosaccharide-specific lectin and hence has a more promiscuous binding specificity than either CV-N or SVN (Mori et al., 2005, supra) such a result was not unexpected. Contrarily, pretreatment with CNID-1 did not inhibit GRFT binding to gp120 (FIG. 9D). Of interest is that CV-N was previously shown to inhibit GRFT binding to gp120 (Mori et al., 2005, supra); however in this study, CV-N did not inhibit CNID-1 binding to gp120, further supporting that CNID-1 might have a distinct interaction with the viral glycoproteins than the above antiviral proteins.

These studies together further support that CNID-1 can be used in combination with other microbicides, such as CV-N.

Example 7

This example demonstrates the expression, purification, and analysis of recombinant cnidarin.

Initial experiments of expression of rCNID-1-Trx in the *E. coli* strain BL21(DE3) with 1M IPTG induction at 37° C. showed that the majority of rCNID-1-Trx accumulated in the inclusion bodies in an insoluble form. Attempts at extracting and refolding the rCNID-1-Trx from the inclusion bodies, however, led to either inactive (absence of $CaCl_2$) or low-to-partially active ($CaCl_2$ presence) CNID-1. This was the case even at lower induction and growth temperatures (25° C. and 18° C.) investigated.

In an effort to increase the expression of soluble protein in order to optimize the production or rCNID-1-Trx, expression of rCNID-1-Trx in the *E. coli* BL21-CodonPlus(DE3)-RIPL strain (engineered by the manufacturer to contain extra copies of genes that encode the tRNAs) was examined. This resulted in a significant increase in expression of soluble protein.

Recombinant rCNID-1-Trx was purified on a Talon Superflow metal affinity column with an estimated yield of 20-25 mg rCNID-1-Trx per liter of culture media. SDS-PAGE analysis shows rCNID-1-Trx at the expected size of approximately 35 kDa, with approximately 80% purity. When recombinant CNID-1 (rCNID-1-Trx), which was His-tagged and fused with thioredoxin to increase rCNID-1 accumulation in the soluble fraction, was cleaved to remove the tag and thioredoxin, truncated forms of CNID-1 were produced (e.g., loss of ~2-6 kDa from the C-terminus corresponding to about 15 to about 60 amino acids).

In particular, when digested by recombinant enterokinase and purified, truncated forms of rCNID-1 (~14-16 kDa) were seen on SDS-PAGE and confirmed by LC-MS analysis. These rCNID-1 truncated forms, when tested for anti-HIV activity using the T-tropic laboratory strain (HIV-$1_{RF}$) in CEM-SS cells, had low to moderate nanomolar activity ($EC_{50}$ values of 45-150 nM) which was reduced from the picomolar activity of native CNID-1. The biological activity of rCNID-1 was further confirmed by the ELISA studies which show that undigested rCNID-1-Trx binds to HIV-1 glycoproteins, gp120 (FIG. 5).

Since the truncated forms had potent nanomolar activity albeit lower than the native CNID-1 but significant enough to show that CNID-1 has anti-HIV potential, it is apparent that smaller versions of the cnidarins can function as anti-HIV agents and that domains outside the truncated C-terminal regions are important for antiviral activity.

Example 8

This example demonstrates the antiviral activity of CNID-1, CNID-2, and CNID-3.

Isolated and phytohaemagglutinin (PHA)-stimulated human PBMCs were incubated with the appropriate concentration of HIV-$1_{US/92/727}$ and 9 concentrations (serially diluted log) of CNID-1, CNID-2, or CNID-3 in triplicate. The cultures were incubated for 7 days at 37° C./5% $CO_2$. Efficacy of the compounds was evaluated by measuring the amount of reverse transcriptase in the culture supernatant and toxicity was evaluated using XTT to measure cell viability. AZT was evaluated in parallel as an assay control.

The half maximal effect concentration (EC50), toxic concentration 50% (TC50), and therapeutic index (TI) for the cnidarin proteins and AZT are described in Table 3. This data confirms the low nanomolar to picomolar antiviral activity of cnidarin proteins described in Example 3.

TABLE 3

Anti-HIV Evaluation of Cnidarin proteins in Human PBMCs

| | HIV-$1_{US/92/727}$ | | |
|---|---|---|---|
| Compound | $EC_{50}$ | $TC_{50}$ | TI |
| AZT | 1.88 nM | >1000 nM | >531.91 |
| CNID-1 | 0.0427 µg/mL | >0.5 µg/mL | >11.71 |
| CNID-2 | 0.0130 µg/mL | >0.5 µg/mL | >38.46 |
| CNID-3 | 0.0160 µg/mL | >0.5 µg/mL | >31.25 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A conjugate comprising an anti-viral polypeptide comprising SEQ ID NO: 1 or 3, or comprising SEQ ID NO: 1 or 3 with a C-terminal truncation of 1-60 amino acids and at least one additional component, wherein the additional component is polyethylene glycol, albumin, dextran, a toxin, an immunological reagent, a virus, a viral envelope glycoprotein, an antiviral agent, or a solid support matrix.

2. The conjugate of claim 1, wherein the anti-viral polypeptide comprises SEQ ID NO: 1 with a C-terminal truncation of 1-60 amino acids.

3. The conjugate of claim 1, wherein the anti-viral polypeptide comprises SEQ ID NO: 3 with a C-terminal truncation of 1-60 amino acids.

4. A composition comprising a carrier and the conjugate of claim 1.

5. A method of producing an anti-viral polypeptide comprising SEQ ID NO: 1 or 3 or comprising SEQ ID NO: 1 or 3 with a C-terminal truncation of 1-60 amino acids, which method comprises (1) obtaining a cnidarin from Synthecium, (2) sequencing the cnidarin, (3) synthesizing corresponding DNA, (4) subcloning the DNA into an expression vector, (5) delivering the vector into a polypeptide-producing cell and (6) allowing the cell to express the anti-viral polypeptide in a cell.

6. A method of inhibiting HIV-1 replication in a host comprising administering a composition comprising an anti-viral polypeptide comprising SEQ ID NO: 1 or 3, or comprising SEQ ID NO: 1 or 3 with C-terminal truncation of 1-60 amino acids, wherein the administration of the polypeptides inhibits viral replication.

7. The method of claim 6, wherein the polypeptide comprises SEQ ID NO: 1 with a C-terminal truncation.

8. The method of claim 6, wherein the polypeptide comprises SEQ ID NO: 1.

9. The method of claim 6, wherein the polypeptide comprises SEQ ID NO: 3 with a C-terminal truncation.

10. The method of claim 6, wherein the polypeptide comprises SEQ ID NO: 3.

11. The method of claim 6, wherein the composition comprising the anti-viral polypeptide comprises at least one additional component, wherein the additional component is polyethylene glycol, albumin, dextran, a toxin, an immunological reagent, a virus, a viral envelope glycoprotein, an antiviral agent, or a solid support matrix.

* * * * *

SEQUENCE LISTING

<160> NUMBER OF SEQ ID NOS: 3

<210> SEQ ID NO 1
<211> LENGTH: 172
<212> TYPE: PRT
<213> ORGANISM: Artificial Sequence
<220> FEATURE:
<223> OTHER INFORMATION: Synthetic

<400> SEQUENCE: 1

```
Gly Arg Ala Thr Leu Gly Gln Leu Lys Thr Ser Thr Ile Pro Pro Val
1               5                  10                  15

Thr Phe Asp Val Pro Phe Asp Gly Ala Asn Ile Pro Gln Asp Val Arg
            20                  25                  30

Phe Thr Ile Ala Thr Val Asn Gly Gly Lys Gly Ala Leu Tyr Asn Ala
        35                  40                  45

Glu Leu Gly Glu Ser Ala Gly His Thr Ile Val Leu Glu Ser Asp Gly
50                  55                  60

Asp His Pro Ile Pro Gly Thr Phe Asp Pro Lys Ser Gly Arg Gly Leu
65                  70                  75                  80

Asp Tyr Leu Pro Arg Gly Leu Val Leu Phe Ser Ser His Asn Tyr Val
                85                  90                  95

Gly Asn Met Lys Met Tyr Thr Glu Pro Asp Ser Asp Ile Thr Ala Asp
            100                 105                 110

Phe Pro Pro Gly Thr Pro Phe Gly Val Ser Ser Ala Ile Thr Gly Glu
        115                 120                 125

Gly Ser Ala Phe Gln Leu Asn Thr Gly Ile Asp His Thr Gly Glu Phe
    130                 135                 140

Glu Ile Ile Pro Pro Asn Thr Lys Arg Asn Leu Ala Gly Val Phe Asp
145                 150                 155                 160

Asn Glu Ile Arg Ser Val Ser Pro Thr Gly Gly Lys
                165                 170
```

<210> SEQ ID NO 2
<211> LENGTH: 168
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(44)
<223> OTHER INFORMATION: Xaa can be any naturally occurring amino acid
<220> FEATURE:
<221> NAME/KEY: misc_feature
<222> LOCATION: (127)..(129)
<223> OTHER INFORMATION: Xaa can be any naturally occurring amino acid
<220> FEATURE:
<221> NAME/KEY: misc_feature
<222> LOCATION: (149)..(151)
<223> OTHER INFORMATION: Xaa can be any naturally occurring amino acid

<400> SEQUENCE: 2

```
Asp Val Gly Leu Pro Lys Thr Ala Thr Ile Pro Pro Val Leu Phe Gln
1               5                  10                  15

Val Pro Ala Asp Gly Ala Tyr Ile Met Gln Ile Asn Glu Phe Thr Ile
            20                  25                  30

Ala Thr Val Asn Gly Gly Lys Xaa Xaa Xaa Xaa Xaa Asn Phe Phe Gly
        35                  40                  45

Pro Ser Ile Asp Asp Ser Ile Val Leu Glu Ser Asn Gly Asp His Pro
50                  55                  60
```

```
Ile Gln Asp Phe Ala Val Glu Met Pro Pro Asn Glu Asp Tyr Glu Pro
 65                  70                  75                  80

Gly Gly Leu Leu Asp Phe Ser Ser His Asn Tyr Val Gly Asn Met Lys
                 85                  90                  95

Met Tyr Thr Glu Ala Val Asn Asp Ile Thr Ala Glu Phe Pro Pro Gln
            100                 105                 110

Thr Pro Leu Gly Val Ser Ser Ala Ile Thr Trp Glu Gly Val Xaa Xaa
            115                 120                 125

Xaa Leu Ser Val Gly Leu Asn His Ala Asp Pro Ser Gln Ile Met Pro
    130                 135                 140

Pro Asn Glu Lys Xaa Xaa Xaa Ala Gly Val Phe Asp Asn Glu Phe Arg
145                 150                 155                 160

Ser Val Ser Pro Thr Gly Gly Lys
                165
```

<210> SEQ ID NO 3
<211> LENGTH: 170
<212> TYPE: PRT
<213> ORGANISM: Artificial Sequence
<220> FEATURE:
<223> OTHER INFORMATION: Synthetic

<400> SEQUENCE: 3

```
Gly Lys Ser Ala Tyr Pro Gly Gln Ile Thr Ser Asp Val Pro Phe Val
  1               5                  10                  15

Thr Phe Asp Val Pro Phe Asp Gly Val Asn Ile Pro Gln Asp Val Arg
                 20                  25                  30

Phe Thr Ile Ala Thr Val Asn Gly Gly Lys Leu Ala Leu Tyr Asn Ala
             35                  40                  45

Lys Leu Gly Asp Pro Ala Asn Asn Thr Ile Val Leu Glu Ser Asp Gly
     50                  55                  60

Asp His Pro Ile Pro Gly Thr Phe Asp Pro Lys Gly Arg Gly Leu
 65                  70                  75                  80

Asp Tyr Ala Phe Gly Gly Leu Leu Leu Phe Ser Phe His Asn Phe Val
                 85                  90                  95

Gly His Lys Lys Leu Tyr Arg Glu Pro Asp Ser Asp Ile Thr Ala Asp
            100                 105                 110

Phe Pro Pro Gly Leu Gly Gly Ser Ser Ala Ile Thr Gly Glu Gly Ser
            115                 120                 125

Thr Val Gln Leu Tyr Thr Gly Ile Asp Phe Thr Gly Ile Ser Glu Ile
    130                 135                 140

Met Pro Val Asn Thr Lys Arg Asn Phe Val Val Ala Phe Gly Asn Glu
145                 150                 155                 160

Phe Lys Ser Val Ser Pro Thr Gly Gly Gly
                165                 170
```